(12) United States Patent
Sundermann et al.

(10) Patent No.: US 7,173,045 B2
(45) Date of Patent: *Feb. 6, 2007

(54) 4-AMINOMETHYL-1-ARYL-CYCLOHEXYLAMINE COMPOUNDS

(75) Inventors: Bernd Sundermann, Aachen (DE); Hans Schick, Berlin (DE); Claudia Hinze, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/125,359

(22) Filed: May 10, 2005

(65) Prior Publication Data

US 2005/0245593 A1    Nov. 3, 2005

Related U.S. Application Data

(63) Continuation of application No. PCT/EP03/12313, filed on Nov. 5, 2003.

(30) Foreign Application Priority Data

Nov. 11, 2002  (DE) ................................ 102 52 665

(51) Int. Cl.
| | |
|---|---|
| C07C 335/12 | (2006.01) |
| C07C 275/06 | (2006.01) |
| C07D 401/04 | (2006.01) |
| C07D 209/20 | (2006.01) |
| A61K 31/454 | (2006.01) |
| A61K 31/404 | (2006.01) |
| A61K 31/17 | (2006.01) |
| C07C 335/02 | (2006.01) |

(52) U.S. Cl. ...................... 514/330; 546/201; 548/496; 548/504; 564/27; 564/47; 514/419; 514/595

(58) Field of Classification Search ................ 514/330, 514/419, 595; 546/201; 548/496, 504; 564/27, 564/47

See application file for complete search history.

(56) References Cited

U.S. PATENT DOCUMENTS 4,483,991 A  * 11/1984  Freed .................. 546/189
6,057,338 A    5/2000  Yang et al.
6,172,067 B1   1/2001  Ito et al.
2005/0277674 A1 * 12/2005  Hinze et al. ............. 514/323

FOREIGN PATENT DOCUMENTS

| DE | 699 03 953 T2 | 3/2003 |
|---|---|---|
| WO | WO 98/28326 | 7/1998 |
| WO | WO 01/87838 A1 | 11/2001 |
| WO | WO 02/085357 A1 | 10/2002 |
| WO | WO 02/090317 A1 | 11/2002 |
| WO | WO02090317 A1 * | 11/2002 |

OTHER PUBLICATIONS

Bregola, et al."Involvement of the Neuropeptide Orphanin FQ/Nociceptin in Kainate and Kindling Seizures and Epileptogenesis" Epilepsia, 43(Suppl. 5): 18-19 (2002).*
Inoue et al., "Pronociceptive Effects of Nociceptin/Orphanin FQ (13-17) at Peripheral and Spinal Level in Mice" J. Pharm. Experimental Therapeutics, 299(1), 213-219 (2001).*
Calo et al. "Pharmacology of Nociceptin and its Receptor: A Novel Therapeutic Target" British J. Pharm. 129, 1261-1283 (2000).*
Abdulla and Smith, J. Neurosci. 18, 1998, p. 9685-9694.
Ardati et al., Mol. Pharmacol., 51, 1997, p. 816-824.
Calo et al., Br. J. Pharmacol., 129, 2000, 1261-1283.
Jenck et al., Proc. Natl. Acad. Sci. USA 94, 1997, 14854-14858.
King et al., Neurosci. Lett., 223, 1997, 113-116.
Lednicer et al., J. Med. Chem., 23, 1980, 424-430.
Manabe et al., Nature, 394, 1997, p. 577-581.
Meunier et al., Nature 377, 1995, p. 532-535.
Mogil et al., Neuroscience 75, 1996, p. 333-337.
Nishi et al., EMBO J., 16, 1997, p. 1858 1864.
Reinscheid et al., Science 270, 1995, p. 792-794.

* cited by examiner

Primary Examiner—Joseph K. McKane
Assistant Examiner—Nyeemah A. Grazier
(74) Attorney, Agent, or Firm—Crowell & Moring LLP

(57) ABSTRACT

The invention concerns 4-aminomethyl-1-aryl-cyclohexylamine compounds, methods for producing same, pharmaceutical formulations containing said compounds and the use of 4-aminomethyyl-1-aryl-cyclohexylamine compounds for producing medicines and in related methods of treatment.

49 Claims, No Drawings

4-AMINOMETHYL-1-ARYL-CYCLOHEXYLAMINE COMPOUNDS

CROSS REFERENCE TO RELATED APPLICATIONS

This application is a continuation of International Patent Application No. PCT/EP2003/012313, filed Nov. 5, 2003, designating the United States of America, and published in German as WO 2004/043899 A1, the entire disclosure of which is incorporated herein by reference. Priority is claimed based on Federal Republic of Germany Patent Application No. 102 52 665.6, filed Nov. 11, 2002.

FIELD OF THE INVENTION

The present invention relates to 4-aminomethyl-1-aryl-cyclohexylamine compounds, to processes for their preparation, to pharmaceutical formulations comprising these compounds, and to the use of 4-aminomethyl-1-aryl-cyclohexylamine compounds in the preparation of pharmaceutical formulations and related methods of treatment.

BACKGROUND OF THE INVENTION

The heptadecapeptide nociceptin is an endogenous ligand of the ORL1 (opioid-receptor-like) receptor (Meunier et al., Nature 377, 1995, p. 532–535) which belongs to the family of the opioid receptors and is to be found in many regions of the brain and of the spinal cord and exhibits high affinity for the ORL1 receptor. The ORL1 receptor is homologous with the μ, κ and δ opioid receptors, and the amino acid sequence of the nociceptin peptide exhibits a strong similarity with those of the known opioid peptides. The activation of the receptor induced by nociceptin leads, via coupling with $G_{i/o}$ proteins, to inhibition of adenylate cyclase (Meunier et al., Nature 377, 1995, p. 532–535).

After intercerebroventicular administration, the nociceptin peptide exhibits pronociceptive and hyperalgesic activity in various animal models (Reinscheid et al., Science 270, 1995, p. 792–794). These findings can be explained as inhibition of stress-induced analgesia (Mogil et al., Neuroscience 75, 1996, p. 333–337). In this connection, nociceptin has also been shown to have anxiolytic activity (Jenck et al., Proc. Natl. Acad. Sci. USA 94, 1997, 14854–14858).

On the other hand, nociceptin has also been shown to have an antinociceptive effect in various animal models, especially after intrathecal administration. Nociceptin has an antinociceptive action in various models of pain, for example in the tail-flick test in the mouse (King et al., Neurosci. Lett., 223, 1997, 113–116). In models for neuropathic pain, it has likewise been possible to demonstrate an antinociceptive action for nociceptin, which is of particular interest in that the effectiveness of nociceptin increases after axotomy of spinal nerves. This is in contrast to conventional opioids, whose effectiveness diminishes under these conditions (Abdulla and Smith, J. Neurosci., 18, 1998, p. 9685–9694).

The ORL1 receptor is additionally also involved in the regulation of further physiological and pathophysiological processes. These include inter alia learning and memory formation (Manabe et al., Nature, 394, 1997, p. 577–581), hearing ability (Nishi et al., EMBO J., 16, 1997, p. 1858–1864) and numerous further processes. In an overview article by Calo et al. (Br. J. Pharmacol., 129, 2000, 1261–1283), an overview is given of the indications or biological processes in which the ORL1 receptor plays or with high probability might play a role. Those mentioned are, inter alia: analgesia, stimulation and regulation of food intake, influence on μ-agonists such as morphine, treatment of withdrawal symptoms, reduction of the addictive potential of opioids, anxiolysis, modulation of motor activity, memory disorders, epilepsy; modulation of neurotransmitter secretion, especially of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anoretics, analgesics (also in co-administration with opioids) or nootropics is furthermore discussed.

The possible applications of compounds that bind to the ORL1 receptor and activate or inhibit it are correspondingly many and varied. In addition, opioid receptors such as the μ-receptor and other subtypes play a large part in the therapy of pain as well as in other of the mentioned indications. It is accordingly advantageous if the compounds also exhibit activity in respect of these opioid receptors.

SUMMARY OF THE INVENTION

One object of certain embodiments of the present invention is to provide pharmaceutical formulations that act on the nociceptin/ORL1 receptor system and accordingly are suitable for pharmaceutical formulations, especially for the treatment of the various diseases associated with this system according to the prior art or that are suitable for use in the indications mentioned therein.

The invention accordingly provides 4-aminomethyl-1-aryl-cyclohexylamine derivatives of the general formula I

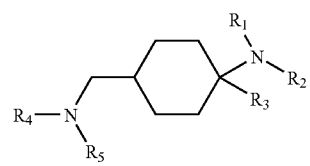

I wherein $R^1$ and $R^2$, independently of one another, represent H; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl and in each case mono- or poly-substituted or unsubstituted, or the radicals $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl and in each case mono- or poly-substituted or unsubstituted, $R^3$ represents $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-4}$-alkyl group and in each case unsubstituted or mono- or poly-substituted, $R^4$ represents H, $C_{1-8}$-alkyl, saturated or unsaturated, branched or unbranched, mono- or poly-substituted or unsubstituted; or $C(X)R^7$, $C(X)NR^7R^8$, $C(X)OR^9$, $C(X)SR^9$, $S(O_2)R^9$, wherein X=O or S, wherein $R^7$ represents H; $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-6}$-alkyl group and in each case unsubstituted or mono- or poly-substituted, $R^8$ represents H, $C_{1-4}$-alkyl, saturated or unsaturated, branched or unbranched, mono- or poly-substituted or unsubstituted, the radicals $R^7$ and $R^8$ together form a ring and represent $CH_2CH_2OCH_2CH_2$, $CH_2CH_2NR^{10}CH_2CH_2$ or $(CH_2)_{3-6}$, wherein $R^{10}$ represents H; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted; or aryl, $C_{3-8}$-cycloalkyl or heteroaryl bonded via $C_{1-3}$-alkyl and in each case mono- or poly-substituted or unsubstituted, $R^9$ represents $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-4}$-alkyl group and in each case unsubstituted or mono- or poly-substituted, $R^5$ represents H; $C_{3-8}$-cycloalkyl, aryl or heteroaryl, in each case unsubstituted or mono- or poly-substituted; a cycloalkyl, aryl or heteroaryl group bonded via a $C_{1-6}$-alkyl group (which may be branched or unbranched, substituted or unsubstituted) and in each case substituted or unsubstituted, wherein $R^4$ and $R^5$ do not simultaneously represent H, or $R^4$ and $R^5$ together form a heterocyclic ring having from 3 to 8 atoms in the ring, saturated or unsaturated, mono- or poly-substituted or unsubstituted, which may optionally be condensed with further rings, optionally in the form of their racemates, their pure stereoisomers, especially enantiomers or diastereoisomers, or in the form of mixtures of the stereoisomers, especially of the enantiomers or diastereoisomers, in any desired mixing ratio;

in the form of their acids or their bases or in the form of their salts, especially the physiologically acceptable salts or salts of physiologically acceptable acids or cations; or in the form of their solvates, especially the hydrates.

All these compounds according to the invention exhibit good binding to the ORL1 receptor, but also to other opiate receptors.

Within the scope of this invention, alkyl and cycloalkyl radicals are understood as meaning saturated and unsaturated (but not aromatic), branched, unbranched and cyclic hydrocarbons, which can be unsubstituted or mono- or polysubstituted. $C_{1-2}$-Alkyl means C1- or C2-alkyl, $C_{1-3}$-alkyl means C1-, C2- or C3-alkyl, $C_{1-4}$-alkyl means C1-, C2-, C3- or C4-alkyl, $C_{1-5}$-alkyl means C1-, C2-, C3-, C4- or C5-alkyl, $C_{1-6}$-alkyl means C1-, C2-, C3-, C4-, C5- or C6-alkyl, $C_{1-7}$-alkyl means C1-, C2-, C3-, C4-, C5-, C6- or C7-alkyl, $C_{1-8}$-alkyl means C1-, C2-, C3-, C4-, C5-, C6-, C7- or C8-alkyl, $C_{1-10}$-alkyl means C1-, C2-, C3-, C4-, C5-, C6-, C7-, C8-, C9- or C10-alkyl and $C_{1-18}$-alkyl means C1-, C2-, C3-, C4-, C5-, C6-, C7-, C8-, C9-, C10-, C11-, C12-, C13-, C14-, C15-, C16-, C17- or C18-alkyl. Furthermore, $C_{3-4}$-cycloalkyl means C3- or C4-cycloalkyl, $C_{3-5}$-cycloalkyl means C3-, C4- or C5-cycloalkyl, $C_{3-6}$-cycloalkyl means C3-, C4-, C5- or C6-cycloalkyl, $C_{3-7}$-cycloalkyl means C3-, C4-, C5-, C6- or C7-cycloalkyl, $C_{3-8}$-cycloalkyl means C3-, C4-, C5-, C6-, C7 or C8-cycloalkyl, $C_{4-5}$-cycloalkyl means C4- or C5-cycloalkyl, $C_{4-6}$-cycloalkyl means C4-, C5- or C6-cycloalkyl, $C_{4-7}$-cycloalkyl means C4-, C5-, C6- or C7-cycloalkyl, $C_{5-6}$-cycloalkyl means C5- or C6-cycloalkyl and $C_{5-7}$-cycloalkyl means C5-, C6- or C7-cycloalkyl. In respect of cycloalkyl, the term also includes saturated cycloalkyls in which one or 2 carbon atoms have been replaced by a hetero atom, S, N or O. However, the term cycloalkyl also includes especially mono- or poly-unsaturated, preferably monounsaturated, cycloalkyls without a hetero atom in the ring, provided the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, $CHF_2$, $CF_3$ or $CH_2OH$, as well as pyrazolinone, oxopyrazolinone, [1,4]dioxane or dioxolane.

In connection with alkyl and cycloalkyl—unless expressly defined elsewhere—the term substituted here is understood within the scope of this invention as meaning the substitution of at least one (optionally also of more than one) hydrogen radical by F, Cl, Br, I, $NH_2$, SH or OH, where "polysubstituted" or "substituted" in the case of polysubstitution is to be understood as meaning that the substitution occurs several times with the same or different substituents both on different and on the same atoms, for example three times on the same C atom, as in the case of $CF_3$, or at different places, as in the case of —CH(OH)—CH═CH—$CHCl_2$. Particularly preferred substituents here are F, Cl and OH. In respect of cycloalkyl, the hydrogen radical can also be replaced by $OC_{1-3}$-alkyl or $C_{1-3}$-alkyl (in each case mono- or poly-substituted or unsubstituted), especially methyl, ethyl, n-propyl, isopropyl, $CF_3$, methoxy or ethoxy.

The term $(CH_3)_{3-6}$ is understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is understood as meaning —$CH_2$—$CH_2$—$CH_2$—$CH_2$— and —$CH_2$—$CH_2$—$CH_2$—$CH_2$—$CH_2$—, etc.

An aryl radical is understood as meaning ring systems having at least one aromatic ring but without hetero atoms in even only one of the rings. Examples are phenyl, naphthyl, fluoranthenyl, fluorenyl, tetralinyl or indanyl, especially 9H-fluorenyl or anthracenyl radicals, which can be unsubstituted or mono- or poly-substituted.

A heteroaryl radical is understood as meaning heterocyclic ring systems having at least one unsaturated ring, which contain one or more hetero atoms from the group nitrogen, oxygen and/or sulfur and can also be mono- or poly-substituted. Examples which may be mentioned from the group of the heteroaryls are furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In connection with aryl and heteroaryl, substituted here is understood as meaning the substitution of the aryl or heteroaryl with $R^{22}$, $OR^{22}$, a halogen, preferably F and/or Cl, a $CF_3$, a CN, an $NO_2$, an $NR^{23}R^{24}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{22}$ here represents H, a $C_{1-10}$-alkyl radical, preferably a $C_{1-6}$-alkyl radical, an aryl or heteroaryl radical or an aryl or heteroaryl radical bonded via $C_{1-3}$-alkyl, saturated or unsaturated, wherein these aryl and heteroaryl radicals may not themselves be substituted by aryl or heteroaryl radicals, the radicals $R^{23}$ and $R^{24}$, which are identical or different, represent H, a $C_{1-10}$-alkyl radical, preferably a $C_{1-6}$-alkyl radical, an aryl radical, a heteroaryl radical or an aryl or heteroaryl radical bonded via $C_{1-3}$-alkyl, saturated or unsaturated, wherein these aryl and heteroaryl radicals may not themselves be substituted by aryl or heteroaryl radicals, or the radicals $R^{23}$ and $R^{24}$ together represent $CH_2CH_2OCH_2CH_2$, $CH_2CH_2NR^{25}CH_2CH_2$ or $(CH_2)_{3-6}$, and the radical $R^{25}$ represents H, a $C_{1-10}$-alkyl radical, preferably a $C_{1-6}$-alkyl radical, an aryl or heteroaryl radical or an aryl or heteroaryl radical bonded via $C_{1-3}$-alkyl, saturated or unsaturated, wherein these aryl and heteroaryl radicals may not themselves be substituted by aryl or heteroaryl radicals.

The term salt is understood as meaning any form of the active ingredient according to the invention in which the active ingredient assumes an ionic form or is charged and is coupled with a counter-ion (a cation or anion) or is in solution. The term is also understood as meaning complexes of the active ingredient with other molecules and ions, especially complexes complexed via ionic interactions. In particular, the term is understood as meaning (and this is also a preferred embodiment of this invention) physiologically acceptable salts, especially physiologically acceptable salts with cations or bases and physiologically acceptable salts with anions or acids or also a salt formed with a physiologically acceptable acid or a physiologically acceptable cation.

The term of the physiologically acceptable salt with anions or acids is understood within the scope of this invention as meaning salts of at least one of the compounds according to the invention—in most cases protonated, for example at the nitrogen—as the cation with at least one anion, which are physiologically—especially when used in humans and/or mammals—acceptable. In particular, the term is understood within the scope of this invention as meaning the salt formed with a physiologically acceptable acid, namely salts of the particular active ingredient with inorganic or organic acids which are physiologically—especially when used in humans and/or mammals—acceptable. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt and the citrate salt are particularly preferred.

The term of the salt formed with a physiologically acceptable acid is understood within the scope of this invention as meaning salts of the particular active ingredient with inorganic or organic acids which are physiologically—especially when used in humans and/or mammals—acceptable. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid.

The term of the physiologically acceptable salt with cations or bases is understood within the scope of this invention as meaning salts of at least one of the compounds according to the invention—in most cases of a (deprotonated) acid—as the anion with at least one cation, preferably an inorganic cation, which are physiologically—especially when used in humans and/or mammals—acceptable. The salts of the alkali metals and alkaline earth metals and also $NH_4^+$ are particularly preferred, but especially (mono-) or (di-)sodium, (mono-) or (di-)potassium, magnesium or calcium salts.

The term of the salt formed with a physiologically acceptable cation is understood within the scope of this invention as meaning salts of at least one of the particular compounds as the anion with at least one inorganic cation which is physiologically—especially when used in humans and/or mammals—acceptable. The salts of the alkali metals and alkaline earth metals and also $NH_4^+$ are particularly preferred, but especially (mono-) or (di-)sodium, (mono-) or (di-)potassium, magnesium or calcium salts.

In a preferred embodiment of the 4-aminomethyl-1-aryl-cyclohexylamine derivatives according to the invention $R^1$ and $R^2$, independently of one another, represent H; $C_{1-8}$-alkyl, saturated or unsaturated, branched or unbranched, mono- or poly-substituted or unsubstituted, or the radicals $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; $C_{1-8}$-alkyl, saturated or unsaturated, branched or unbranched, mono- or poly-substituted or unsubstituted, preferably $R^1$ and $R^2$, independently of one another, represent H; $C_{1-4}$-alkyl, saturated or unsaturated, branched or unbranched, mono- or poly-substituted or unsubstituted; wherein $R^1$ and $R^2$ may not both be H, or the radicals $R^1$ and $R^2$ together form a ring and represent $(CH_2)_{4-5}$, especially R$^1$ and R$^2$, independently of one another, represent methyl or ethyl, or the radicals R$^1$ and R$^2$ together form a ring and represent (CH$_2$)$_5$.

Particular preference is given to 4-aminomethyl-1-aryl-cyclohexylamine derivatives wherein R$^1$ and R$^2$, independently of one another, represent CH$_3$ or H, wherein R$^1$ and R$^2$ may not simultaneously be H.

Preference is given within the scope of this invention to 4-aminomethyl-1-aryl-cyclohexylamine derivatives wherein R$^3$ represents C$_{3-8}$-cycloalkyl, aryl or heteroaryl, in each case unsubstituted or mono- or poly-substituted; aryl, C$_{3-8}$-cycloalkyl or heteroaryl bonded via a saturated or unsaturated, unbranched, substituted or unsubstituted C$_{1-2}$-alkyl group and in each case unsubstituted or mono- or poly-substituted;

preferably

R$^3$ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or poly-substituted; C$_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched C$_{1-2}$-alkyl group and in each case unsubstituted or mono- or poly-substituted;

especially

R$^3$ represents phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or poly-substituted; phenyl, furyl or thiophenyl bonded via a saturated, unbranched C$_{1-2}$-alkyl group and in each case unsubstituted or mono- or poly-substituted.

Particular preference is given to 4-aminomethyl-1-aryl-cyclohexylamine derivatives wherein R$^3$ represents phenyl, thiophenyl, pyridyl or benzyl, in each case substituted or unsubstituted, particularly preferably phenyl.

Preference is given within the scope of this invention also to 4-aminomethyl-1-aryl-cyclohexylamine derivatives wherein R$^4$ represents H, C(X)R$^7$, C(X)NR$^7$R$^8$, C(X)OR$^9$, C(X)SR$^9$ or S(O$_2$)R$^9$, wherein X=O or S, wherein R$^4$ preferably represents H, C(X)R$^7$ or C(X)NR$^7$R$^8$ wherein X=O, S, and R$^4$ especially represents H or C(O)R$^7$; CONR$^7$R$^8$ or CSNR$^7$R$^8$.

It is preferred for R$^8$ to represent H and R$^7$ to represent a heteroaryl or aryl group bonded via a C$_{1-6}$-alkyl group, particularly preferably phenyl, naphthyl, pyridyl, benzothiophenyl, benzofuranyl, quinolinyl, isoquinolinyl, benzothiazolyl, indolyl and indanyl, in each case substituted or unsubstituted, very particularly preferably phenyl and indolyl, in each case substituted or unsubstituted, particular preference being given according to the invention to unsubstituted phenyl or indolyl, or phenyl or indolyl mono- or di-substituted by methyl, methoxy, chlorine, fluorine or by CF$_3$.

It is also preferred if

R$^4$ and R$^5$ together form a heterocyclic ring having from 3 to 8 atoms in the ring, saturated or unsaturated; mono- or poly-substituted or unsubstituted, preferably having from 5 to 7 atoms in the ring, of which, in addition to the compulsory N, from 0 to 1 further hetero atoms, selected from N, S and O, are present in the ring;

wherein the heterocyclic ring formed by R$^4$ and R$^5$ together may optionally be condensed with further rings, preferably with aromatic and/or heteroaromatic rings, it being possible for these rings to be condensed with further aromatic and/or heteroaromatic rings.

Preference is additionally given within the scope of this invention to 4-aminomethyl-1-aryl-cyclohexylamine derivatives wherein R$^5$ represents H, C$_{3-8}$-cycloalkyl, aryl or heteroaryl, in each case unsubstituted or mono- or poly-substituted; preferably R$^5$ represents H; cyclobutyl, cyclopropyl, cyclopentyl, cyclohexyl, cycloheptyl, cyclooctyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthyl, pyrazolinonyl, oxopyrazolinonyl, dioxolanyl, quinolinyl, isoquinolinyl, phthalazinyl or quinazolinyl, in each case unsubstituted or mono- or poly-substituted;

and especially

R$^5$ represents H, cyclopentyl, cyclohexyl, indolyl, naphthyl, benzofuranyl, benzothiophenyl, indanyl, phenyl, thiophenyl, furyl and pyridyl, in each case unsubstituted or mono- or poly-substituted.

Preference is further given to 4-aminomethyl-1-aryl-cyclohexylamine derivatives wherein R$^5$ represents an aryl or heteroaryl group bonded via a C$_{1-6}$-alkyl group (which may be branched or unbranched, substituted or unsubstituted), which aryl or heteroaryl group in each case may be substituted or unsubstituted, the aryl or heteroaryl group particularly preferably being a phenyl, indolyl, naphthyl, benzofuranyl, benzothiophenyl, indanyl, thiophenyl, furyl, pyridyl, pyrrolyl, pyrazinyl, pyrimidyl, quinolinyl or isoquinolinyl group, in each case unsubstituted or mono- or poly-substituted; very particularly preferably phenyl or indolyl, in each case unsubstituted or mono- or poly-substituted; or especially unsubstituted phenyl or indolyl, or phenyl or indolyl mono- or di-substituted by methyl, methoxy, chlorine, fluorine or by CF$_3$.

It is preferred for the C$_{1-6}$-alkyl group via which an aryl or heteroaryl group is bonded as part of R$^5$ to be substituted by H, C$_{1-4}$-alkyl, saturated or unsaturated, branched or unbranched, mono- or poly-substituted or unsubstituted; or C(O)O—C$_{1-4}$-alkyl, saturated or unsaturated, branched or unbranched, mono- or poly-substituted or unsubstituted;

preferably substituted by H, CH$_3$, C$_2$H$_5$ and C(O)O—CH$_3$ and especially by H or CH$_3$.

Very particular preference is given also to 4-aminomethyl-1-aryl-cyclohexylamine derivatives from the group (4-{[(1H-indol-3-ylmethyl)amino]methyl}-1-phenylcyclohexyl)dimethylamine dihydrochloride, non-polar diastereoisomer, (4-{[(1H-indol-3-ylmethyl)amino]methyl}-1-phenylcyclohexyl)dimethylamine dihydrochloride, polar diastereoisomer, (4-{[2-(1H-indol-3-yl)-1-methylethylamino]methyl}-1-phenylcyclohexyl)dimethylamine dihydrochloride, non-polar diastereoisomer, (4-{[2-(1H-indol-3-yl)-1-methylethylamino]methyl}-1-phenylcyclohexyl)dimethylamine dihydrochloride, polar diastereoisomer, (4-{[2-(1H-indol-3-yl)ethylamino]methyl}-1-phenylcyclo-
hexyl)dimethylamine dihydrochloride, non-polar diaste-
reoisomer,
(4-{[2-(1H-indol-3-yl)ethylamino]methyl}-1-phenylcyclo-
hexyl)dimethylamine dihydrochloride, polar diastereoiso-
mer,
N-(4-dimethylamino-4-phenylcyclohexylmethyl)-4-(1H-in-
dol-3-yl)butyramide hydrochloride, non-polar diastereoi-
somer,
N-(4-dimethylamino-4-phenylcyclohexylmethyl)-4-(1H-in-
dol-3-yl)butyramide hydrochloride, polar diastereoiso-
mer,
N-(4-dimethylamino-4-phenylcyclohexylmethyl)-2-(1H-in-
dol-3-yl)propionamide hydrochloride, non-polar diastere-
oisomer,
5-(1H-indol-3-yl)pentanoic acid (4-dimethylamino-4-phe-
nylcyclohexylmethyl)amide hydrochloride, non-polar
diastereoisomer,
6-(1H-indol-3-yl)hexanoic acid (4-dimethylamino-4-phe-
nylcyclohexylmethyl)amide hydrochloride, non-polar
diastereoisomer,
N-(4-dimethylamino-4-phenylcyclohexylmethyl)-2-(1H-in-
dol-3-yl)acetamide hydrochloride, non-polar diastereoi-
somer,
5-(5-fluoro-1H-indol-3-yl)pentanoic acid (4-dimethy-
lamino-4-phenyl-cyclohexylmethyl)amide citrate, non-
polar diastereoisomer,
5-(5-fluoro-1H-indol-3-yl)pentanoic acid (4-dimethy-
lamino-4-phenyl-cyclohexylmethyl)amide citrate, polar
diastereoisomer,
N-(4-dimethylamino-4-phenylcyclohexylmethyl)-2-indol-
1-yl-acetamide, non-polar diastereoisomer,
N-(4-dimethylamino-4-phenylcyclohexylmethyl)-2-indol-
1-yl-acetamide, polar diastereoisomer,
6-(5-fluoro-1H-indol-3-yl)hexanoic acid (4-dimethylamino-
4-phenylcyclohexylmethyl)amide citrate, polar diastere-
oisomer,
6-(5-fluoro-1H-indol-3-yl)hexanoic acid (4-dimethylamino-
4-phenylcyclohexylmethyl)amide citrate, polar diastere-
oisomer,
N-(4-dimethylamino-4-phenylcyclohexylmethyl)-3-indol-
1-yl-propionamide citrate, non-polar diastereoisomer,
N-(4-dimethylamino-4-phenylcyclohexylmethyl)-3-indol-
1-yl-propionamide citrate, polar diastereoisomer,
4-(5-fluoro-1H-indol-3-yl)butanoic acid (4-dimethylamino-
4-phenylcyclohexylmethyl)amide hydrochloride, non-po-
lar diastereoisomer,
4-(5-fluoro-1H-indol-3-yl)butanoic acid (4-dimethylamino-
4-phenylcyclohexylmethyl)amide hydrochloride, polar
diastereoisomer,
6-(5-chloro-1H-indol-3-yl)hexanoic acid (4-dimethylamino-
4-phenylcyclohexylmethyl)amide hydrochloride, non-po-
lar diastereoisomer,
6-(5-chloro-1H-indol-3-yl)hexanoic acid (4-dimethylamino-
4-phenylcyclohexylmethyl)amide hydrochloride, polar
diastereoisomer,
N-(4-dimethylamino-4-phenylcyclohexyl)-2-(5-fluoro-2-
methyl-1H-indol-3-yl)acetamide citrate, non-polar diaste-
reoisomer,
N-(4-dimethylamino-4-phenylcyclohexyl)-2-(5-fluoro-2-
methyl-1H-indol-3-yl)acetamide citrate, polar diastereoi-
somer,
1-(4-dimethylamino-4-phenylcyclohexylmethyl)-3-(3-phe-
nylpropyl)urea hydrochloride, non-polar diastereoisomer,
1-(4-dimethylamino-4-phenylcyclohexylmethyl)-3-(3-phe-
nylpropyl)urea hydrochloride, polar diastereoisomer,
1-(4-dimethylamino-4-phenylcyclohexylmethyl)-3-[2-(1H-
indol-3-yl)ethyl]urea hydrochloride, polar diastereoiso-
mer,
1-(4-dimethylamino-4-phenylcyclohexylmethyl)-3-[2-(1H-
indol-3-yl)ethyl]urea, non-polar diastereoisomer,
1-(4-dimethylamino-4-phenylcyclohexylmethyl)-3-[2-(1H-
indol-3-yl)-1-methylethyl]urea hydrochloride, non-polar
diastereoisomer,
1-(4-dimethylamino-4-phenylcyclohexylmethyl)-3-[2-(1H-
indol-3-yl)-1-methylethyl]urea hydrochloride, polar dias-
tereoisomer,
1-(4-dimethylamino-4-phenylcyclohexylmethyl)-3-[2-(5-
fluoro-1H-indol-3-yl)ethyl]urea citrate, polar diastereoi-
somer,
1-(4-dimethylamino-4-phenylcyclohexylmethyl)-3-[2-(5-
fluoro-1H-indol-3-yl)ethyl]urea citrate, non-polar diaste-
reoisomer,
4-(5-fluoro-1H-indol-3-yl)piperidine-1-carboxylic acid
(4-dimethylamino-4-phenylcyclohexylmethyl)amide cit-
rate, non-polar diastereoisomer,
4-(5-fluoro-1H-indol-3-yl)piperidine-1-carboxylic acid
(4-dimethylamino-4-phenylcyclohexylmethyl)amide cit-
rate, polar diastereoisomer,
4-(5-methoxy-1H-indol-3-yl)piperidine-1-carboxylic acid
(4-dimethylamino-4-phenylcyclohexylmethyl)amide cit-
rate, non-polar diastereoisomer,
4-(5-methoxy-1H-indol-3-yl)piperidine-1-carboxylic acid
(4-dimethylamino-4-phenylcyclohexylmethyl)amide cit-
rate, polar diastereoisomer,
1-(4-dimethylamino-4-phenylcyclohexylmethyl)-3-[2-(1H-
indol-3-yl)ethyl]thiourea citrate, polar diastereoisomer,
1-(4-dimethylamino-4-phenylcyclohexylmethyl)-3-[2-(1H-
indol-3-yl)ethyl]thiourea citrate, non-polar diastereoiso-
mer,
2-[3-(4-dimethylamino-4-phenylcyclohexylmethyl)thioure-
ido]-3-(1H-indol-3-yl)propionic acid methyl ester citrate,
polar diastereoisomer,
2-[3-(4-dimethylamino-4-phenylcyclohexylmethyl)thioure-
ido]-3-(1H-indol-3-yl)propionic acid methyl ester citrate,
non-polar diastereoisomer, optionally also in the form of a mixture.

The substances according to the invention act, for example, on the ORL1 receptor, which is relevant in connection with various disorders, but also on the μ-opiate receptor, so that they are suitable as a pharmaceutical active ingredient in a pharmaceutical formulation.

Accordingly, the invention further provides pharmaceutical formulations comprising at least one 4-aminomethyl-1-aryl-cyclohexylamine derivative.

In addition to at least one 4-aminomethyl-1-aryl-cyclohexylamine derivative according to the invention, the pharmaceutical formulations according to the invention optionally comprise suitable additives and/or auxiliary substances, that is to say also carrier materials, fillers, solvents, diluents, colourings and/or binders, and can be administered as liquid pharmaceutical formulation forms in the form of injection solutions, drops or juices, as semi-solid pharmaceutical formulation forms in the form of granules, tablets, pellets, patches, capsules, plasters or aerosols. The choice of the auxiliary substances etc. and the amounts thereof to be employed depend on whether the pharmaceutical formulation is to be administered orally, perorally, parenterally, intravenously, intraperitoneally, intradermally, intramuscularly, intranasally, buccally, rectally or locally, for example to the skin, the mucous membranes or in the eyes. Preparations in the form of tablets, coated tablets, capsules, granules, drops, juices and syrups are suitable for oral administration; solutions, suspensions, easily reconstitutable dry formulations and sprays are suitable for parenteral and topical administration and for administration by inhalation. 4-Aminomethyl-1-aryl-cyclohexylamine derivatives according to the invention in a depot, in dissolved form or in a plaster, optionally with the addition of agents which promote penetration through the skin, are suitable preparations for percutaneous administration. Forms of preparation which can be used orally or percutaneously can release the 4-aminomethyl-1-aryl-cyclohexylamine derivatives according to the invention in a delayed manner. Other further active ingredients known to the person skilled in the art can in principle be added to the pharmaceutical formulations according to the invention.

The amount of active ingredient to be administered to the patients varies according to the weight of the patient, the mode of administration, the indication and the severity of the disorder. From 0.005 to 1000 mg/kg, preferably from 0.05 to 5 mg/kg, of at least one 4-aminomethyl-1-aryl-cyclohexylamine derivative according to the invention are usually administered.

For all the above forms of the pharmaceutical formulations according to the invention it is particularly preferred if, in addition to at least one 4-aminomethyl-1-aryl-cyclohexylamine derivative, the pharmaceutical formulation also comprises a further active ingredient, especially an opioid, preferably a potent opioid, especially morphine, or an anaesthetic, preferably hexobarbital or halothane.

In a preferred form of the pharmaceutical formulation, a 4-aminomethyl-1-aryl-cyclohexylamine derivative according to the invention contained therein is present in the form of a pure diastereoisomer and/or enantiomer, in the form of a racemate or in the form of a non-equimolar or equimolar mixture of the diastereoisomers and/or enantiomers.

As can be seen in the introduction from the prior art, the ORL1 receptor has been identified especially in the occurrence of pain. 4-Aminomethyl-1-aryl-cyclohexylamine derivatives according to the invention can accordingly be used in the preparation of a pharmaceutical formulation for the treatment of pain, especially of acute, neuropathic or chronic pain.

Accordingly, the invention relates further to the use of a 4-aminomethyl-1-aryl-cyclohexylamine derivative according to the invention in the preparation of a pharmaceutical formulation for the treatment of pain, especially of acute, visceral, neuropathic or chronic pain.

Accordingly, the invention relates further to the use of a 4-aminomethyl-1-aryl-cyclohexylamine derivative according to the invention in the preparation of a pharmaceutical formulation for the treatment of anxiety, stress and stress-associated syndromes, depression, epilepsy, Alzheimer's disease, senile dementia, general cognitive dysfunctions, learning and memory disorders (as a nootropic), withdrawal symptoms, alcohol and/or drug and/or pharmaceutical formulation abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration in the case of treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for the treatment of withdrawal symptoms and/or for reducing the addictive potential of opioids.

In one of the above uses it may be preferable for a 4-aminomethyl-1-aryl-cyclohexylamine derivative used to be in the form of a pure diastereoisomer and/or enantiomer, in the form of a racemate or in the form of a non-equimolar or equimolar mixture of the diastereoisomers and/or enantiomers.

The invention further provides a method of treating, especially in one of the above-mentioned indications, a non-human mammal or human requiring the treatment of pain, especially chronic pain, by administration of a therapeutically effective dose of a 4-aminomethyl-1-aryl-cyclohexylamine derivative according to the invention, or of a pharmaceutical formulation according to the invention.

The invention further provides a process for the preparation of the 4-aminomethyl-1-aryl-cyclohexylamine derivatives according to the invention, as indicated in the following description and examples. Particularly suitable is a process for the preparation of a 4-aminomethyl-1-aryl-cyclohexylamine derivative according to the invention that comprises the following steps, wherein $R^1$, $R^2$, $R^3$, $R^4$ and $R^5$ have the meaning given for compounds of formula I according to the invention and $R^{01}$ and $R^{02}$, independently of one another, represent a protecting group or have the meaning given for $R^1$ and $R^2$ for compounds of formula I according to the invention:

Process I:

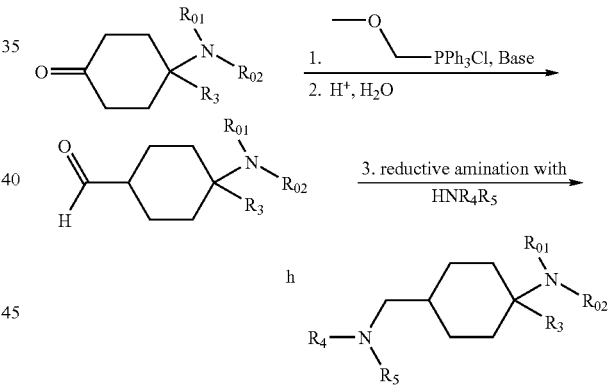

Methoxymethyltriphenylphosphonium chloride is reacted first with a strong base, for example sodium hydride or butyllithium, and then with a 4-aminocyclohexanone, and the methyl vinyl ether formed as intermediate is converted under acidic aqueous conditions, for example with hydrochloric acid or sulfuric acid, into the corresponding 4-aminocyclohexanecarbaldehyde, which is converted into the 4-aminomethyl-1-arylcyclohexylamine derivatives according to the invention with an amine $HNR^4R^5$ under conditions known to the person skilled in the art for reductive amination, for example with hydrides such as sodium or lithium borohydride, sodium cyanoborohydride, sodium triacetoxyborohydride, diisobutylaluminium hydride, lithium tri-(sec.-butyl)borohydride (L-Selectride®) or lithium aluminium hydride, optionally in the presence of Lewis acids, for example $ZnCl_2$, $Ni(OAc)_2$ or $CoCl_2$, or by catalytic hydrogenation on noble metals, for example palladium or platinum, with hydrogen as reducing agent.

Process II:

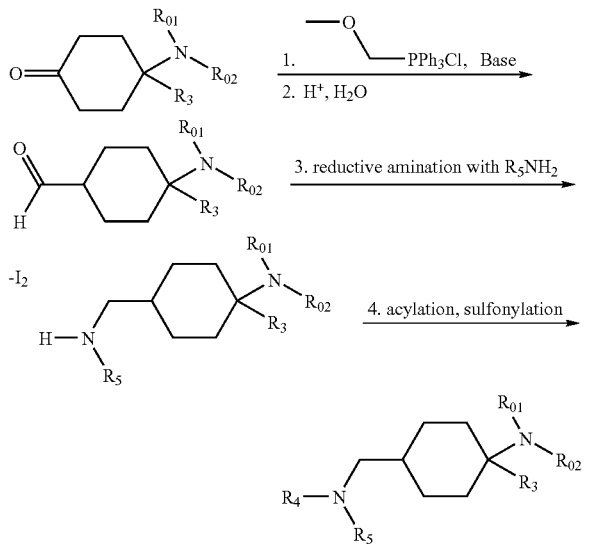

Alternatively, 4-aminocyclohexanecarbaldehydes prepared according to Process I can be reacted with $H_2NR^5$ under conditions known to the person skilled in the art for reductive amination, for example with hydrides such as sodium or lithium borohydride, sodium cyanoborohydride, sodium triacetoxyborohydride, diisobutylaluminium hydride, lithium tri-(sec.-butyl)borohydride (L-Selectride®) or lithium aluminium hydride, optionally in the presence of Lewis acids, for example $ZnCl_2$, $Ni(OAc)_2$ or $CoCl_2$, or by catalytic hydrogenation on noble metals, for example palladium or platinum, with hydrogen as reducing agent, to form a secondary amine, which is then optionally reacted with a carboxylic or sulfonic acid halide or anhydride in the presence of organic or inorganic bases, for example sodium methoxide, triethylamine or diisopropylamine, to form 4-aminomethyl-1-aryl-cyclohexylamine derivatives according to the invention.

Process III:

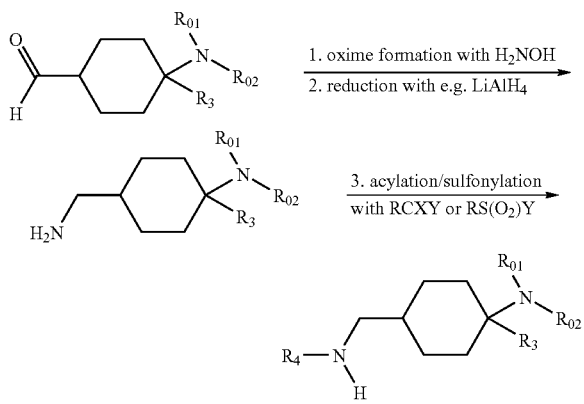

It is additionally possible to react a 4-aminocyclohexanecarbaldehyde with hydroxylamine to form the oxime, to reduce the latter to the amine with a reducing agent, for example lithium aluminium hydride, and to acylate the resulting product with a carboxylic or sulfonic acid halide or anhydride in the presence of organic or inorganic bases, for example sodium methoxide, triethylamine or diisopropylethylamine, to form 4-aminomethyl-1-aryl-cyclohexylamine derivatives according to the invention.

Process IV:

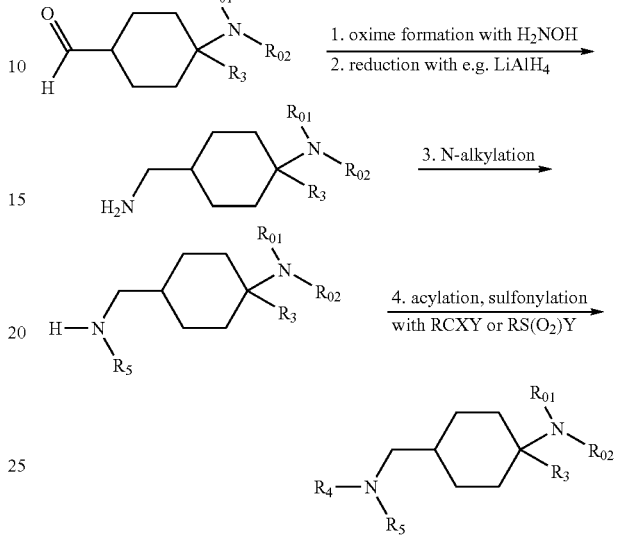

Alternatively, products of the oxime reduction obtained analogously to Process III can be reacted first with $R^5$ halides in the presence of organic or inorganic bases and then optionally with a carboxylic or sulfonic acid halide or anhydride in the presence of organic or inorganic bases, for example sodium methoxide, triethylamine or diisopropylethylamine, to form 4-aminomethyl-1-aryl-cyclohexylamine derivatives according to the invention.

For the preparation of ureas ($R^4$=$C(O)NR^7R^8$), analogously to the processes described above—in addition to other methods known to the person skilled in the art—one of the two amine components $HNR^7R^8$ or

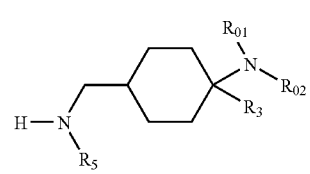

to be linked is advantageously first converted into a chloroformic acid ester, preferably the corresponding phenyl ester, and then reacted with the second amine component (see e.g. Examples 27 and 28 or 35 and 36). This reaction can also be carried out with microwave irradiation.

For the preparation of thioureas ($R^4$=$C(S)NR^7R^8$), analogously to the processes described above—in addition to other methods known to the person skilled in the art—one of the two amine components $HNR^7R^8$ or to be linked is advantageously first converted into an isothiocyanate with thiophosgene and then reacted with the second amine component (see Examples 39 to 42).

The preparation of suitable 4-aminocyclohexanones is known from the literature (Lednicer et al., J. Med. Chem., 23, 1980, 424–430; WO 0290317).

Isolation of the compounds according to the invention by column chromatography with silica gel as the stationary phase results in separation of the diastereoisomers of different polarities. On the basis of the elution time in the separation these have been characterised as "the most non-polar diastereoisomer" (shortest elution time) to "the most polar diastereoisomer" (longest elution time).

EXAMPLES

The following examples serve to explain the invention in more detail, but do not limit the general inventive idea.

The yields of the compounds prepared have not been optimised.

All temperatures are uncorrected.

The term "ether" means diethyl ether, "EE" means ethyl acetate, "DCM" means dichloromethane, "DMF" means dimethylformamide, "DMSO" means dimethyl sulfoxide and "THF" means tetrahydrofuran. The term "equivalents" means substance amount equivalents, "m.p." means melting point or melting range, "decomp." means decomposition, "RT" means room temperature, "abs." means absolute (anhydrous), "rac." means racemic, "conc." means concentrated, "min." means minutes, "h" means hours, "d" means days, "vol. %" means percent by volume, "wt. %" means percent by weight and "M" is the concentration stated in mol./l.

Silica gel 60 (0.040–0.063 mm) from E. Merck, Darmstadt, was employed as the stationary phase for the column chromatography.

The thin-layer chromatography analyses were carried out with HPTLC pre-coated plates, silica gel 60 F 254, from E. Merck, Darmstadt.

The mixing ratios of mobile phases for chromatography analyses are always stated in volume/volume.

Example 1

(4-{[(1H-Indol-3-ylmethyl)amino]methyl}-1-phenylcyclohexyl)dimethylamine dihydrochloride, non-polar diastereoisomer Under argon, methoxymethyltriphenylphosphonium chloride (6.3 g, 18.4 mmol.) was dissolved in DMF (25 ml), and sodium hydride (60% in mineral oil, 737 mg, 18.4 mmol.) was added. 4-Dimethylamino-4-phenylcyclohexanone (2.0 g, 9.2 mmol.), dissolved in 25 ml of DMF, was added dropwise in the course of 30 min., and the suspension was stirred for 3 d at RT. For working up, the suspension was slowly poured into ice-water-cooled 2M HCl (50 ml), stirred for 2 h at RT and then extracted with ether (5×25 ml) and EE (6×20 ml). The aqueous phase was then adjusted to pH 10–11 with 1M NaOH and extracted with EE (5×20 ml). The combined extracts were dried over sodium sulfate, filtered and concentrated. The residue was 4-dimethylamino-4-phenylcyclohexanecarbaldehyde (2.0 g of brown oil) in the diastereoisomeric ratio 55:45 ($^1$H-NMR).

C-(1H-Indol-3-yl)-methylamine (292 mg, 2 mmol.) and 4-dimethylamino-4-phenylcyclohexanecarbaldehyde (463 mg, 2 mmol.) were dissolved, under argon, in abs. 1,2-dichloroethane (20 ml). Sodium triacetoxyborohydride (600 mg, 2.8 mmol.) was added to this mixture, and stirring was carried out for 24 h at RT. For working up, the mixture was concentrated and 1M HCl (20 ml) and ether (40 ml) were added thereto. The aqueous phase was washed with ether (2×20 ml), adjusted to pH 11 with 5M NaOH, diluted with water (10 ml) and extracted with EE (3×20 ml). The combined EE extracts were dried, filtered and concentrated. The resulting crude product, a mixture of the two diastereoisomeric target compounds, was purified by chromatography on silica gel with methanol/conc. ammonia solution (500:1) and separated. The non-polar diastereoisomer of (4-{[(1H-indol-3-ylmethyl)amino]methyl}-1-phenylcyclohexyl)dimethylamine dihydrochloride could be obtained in the form of a brown oil in a yield of 83 mg. The oil was dissolved in 2-butanone (5 ml); chlorotrimethylsilane (72 µl, 0.56 mmol.) was added thereto, and stirring was carried out for 2 h at RT. The resulting solid was filtered off with suction. The dihydrochloride of the non-polar diastereoisomer of (4-{[(1H-indol-3-ylmethyl)amino]methyl}-1-phenylcyclohexyl)dimethylamine could thus be obtained in a yield of 48 mg (white solid, m.p. 181–183° C.).

Example 2

(4-{[(1H-Indol-3-ylmethyl)amino]methyl}-1-phenylcyclohexyl)dimethylamine dihydrochloride, polar diastereoisomer In the manner described for Example 1, 124 mg of the polar diastereoisomer of (4-{[(1H-indol-3-ylmethyl)amino]methyl}-1-phenylcyclohexyl)dimethylamine were also obtained in the form of a light-brown oil. The oil was dissolved in 2-butanone (5 ml); chlorotrimethylsilane (108 µl, 853 µmol.) was added thereto, and stirring was carried out for 2 h at RT. The resulting solid was filtered off with suction. The dihydrochloride of the non-polar diastereoisomer of (4-{[(1H-indol-3-ylmethyl)amino]methyl}-1-phenylcyclohexyl)dimethylamine could thus be obtained in a yield of 128 mg (white solid, m.p. 186–190° C.).

Example 3

(4-{[2-(1H-indol-3-yl)-1-methylethylamino]methyl}-1-phenylcyclohexyl)dimethylamine dihydrochloride, non-polar diastereoisomer rac. α-Methyltryptamine (2-(1H-indol-3-yl)-1-methylethylamine, 349 mg, 2 mmol.) was dissolved in abs. 1,2-dichloroethane and, after the addition of 4-dimethylamino-4-phenylcyclohexanecarbaldehyde (463 mg, 2 mmol.), stirring was carried out for 30 min. at RT. Sodium triacetoxyborohydride (660 mg, 3 mmol.) was then added, and stirring was carried out for 4 d at RT. For working up, 1,2-dichloroethane (10 ml), water (15 ml) and 1M HCl (3 ml) were added to the reaction mixture, and the phases were separated. The aqueous phase (pH 5–6) was extracted again with 1,2-dichloroethane (5 ml), adjusted to pH 11 with 5M NaOH and extracted with EE (5×20 ml). The combined EE phases were dried, filtered and concentrated. The resulting diastereoisomeric mixture of the target compound (764 mg) was purified by flash chromatography on silica gel (70 g) and separated (eluant: 1300 ml of methanol/EE/conc. ammonia solution 66:33:0.5). 319 mg (0.82 mmol.) of the non-polar product (360 mg, m.p. 140–147° C.) were dissolved in 2-butanone/acetone (12 ml/2 ml); chlorotrimethylsilane (310 µl, 2.76 mmol.) was added at RT, and stirring was carried out for 2 h. The suspension was cooled for 1 h in an ice bath, and the solid was filtered off with suction, washed with cold 2-butanone and ether and dried. The dihydrochloride of the non-polar diastereoisomer of (4-{[2-(1H-indol-3-yl)-1-methylethylamino]methyl}-1-phenylcyclohexyl)dimethylamine was thus obtained in a yield of 363 mg (white solid, m.p. 165–170° C.).

Example 4

(4-{[2-(1H-Indol-3-yl)-1-methylethylamino]methyl}-1-phenylcyclohexyl)dimethylamine dihydrochloride, polar diastereoisomer In the manner described for Example 3, 324 mg of the polar diastereoisomer of (4-{[2-(1H-indol-3-yl)-1-methylethylamino]methyl}-1-phenylcyclohexyl)dimethylamine were also obtained. 282 mg thereof were dissolved in 2-butanone/acetone (9 ml/1.5 ml); chlorotrimethylsilane (275 μl, 2.2 mmol.) was added and stirring was carried out for 2 h at RT. The resulting solid was filtered off with suction, washed with cold 2-butanone and ether and dried. The dihydrochloride of the non-polar diastereoisomer of (4-{[2-(1H-indol-3-yl)-1-methylethylamino]methyl}-1-phenylcyclohexyl)dimethylamine could thus be obtained in a yield of 290 mg (white solid, m.p. 220–223° C.).

Example 5

(4-{[2-(1H-Indol-3-yl)ethylamino]methyl}-1-phenylcyclohexyl)dimethylamine dihydrochloride, non-polar diastereoisomer Tryptamine (2-(1H-indol-3-yl)ethylamine, 321 mg, 2 mmol.) was dissolved in abs. 1,2-dichloroethane. After the addition of 4-dimethylamino-4-phenylcyclohexanecarbaldehyde (463 mg, 2 mmol.), the mixture was stirred for 1 h at RT. Sodium triacetoxyborohydride (660 mg, 3 mmol.) was then added, and stirring was carried out for 3 d at RT. For working up, 1,2-dichloroethane (10 ml), water (15 ml) and 2M HCl (3 ml) were added to the reaction mixture. After stirring vigorously for 15 min., the phases were separated and the aqueous phase (pH 3) was extracted again with 1,2-dichloroethane (10 ml). 5M NaOH was then added to the aqueous phase (pH 11), followed by extraction with EE (5×20 ml). The combined EE phases were dried, filtered and concentrated. The residue was the still impure diastereoisomeric mixture of the bases of the target product (690 mg, m.p. 56–64° C.), which was purified by flash chromatography on silica gel (70 g) and separated (eluant: 1200 ml of methanol/conc. ammonia solution 99.5:0.5). 220 mg (0.59 mmol.) of the non-polar diastereoisomer of (4-{[2-(1H-Indol-3-yl)ethylamino]methyl}-1-phenylcyclohexyl)dimethylamine (m.p. 78–83° C.) were obtained and were dissolved in 2-butanone; chlorotrimethylsilane (222 μl, 1.8 mmol.) was added at RT, and stirring was carried out for 2 h. The suspension was cooled for 1 h in an ice bath, and the solid was filtered off. The hygroscopic dihydrochloride was washed with cold ether and dried in vacuo. The dihydrochloride of the non-polar diastereoisomer of (4-{[2-(1H-Indol-3-yl)ethylamino]methyl}-1-phenylcyclohexyl)dimethylamine was thus obtained in a yield of 205 mg (white solid, m.p. 170–180° C. with decomposition, rearrangements at only 105° C.).

Example 6

(4-{[2-(1H-Indol-3-yl)ethylamino]methyl}-1-phenylcyclohexyl)dimethylamine dihydrochloride, polar diastereoisomer In the manner described for Example 5, 94 mg (0.25 mmol.) of the polar diastereoisomer of (4-{[2-(1H-indol-3-yl)ethylamino]methyl}-1-phenylcyclohexyl)dimethylamine were also obtained; the latter was dissolved in ethanol (4 ml), and 3.3M ethanolic HCl (227 μl, 0.75 mmol.) were added at RT, followed by stirring for 2 h. The mixture was concentrated to dryness, the residue was suspended in ether and cooled, and the solid was filtered off, washed with cold ether and dried in vacuo. The dihydrochloride of the polar diastereoisomer of (4-{[2-(1H-indol-3-yl)ethylamino]methyl}-1-phenylcyclohexyl)dimethylamine was obtained in a yield of 54 mg (white solid, m.p. 160–165° C. with decomposition; rearrangements at only 100° C.).

Example 7

N-(4-Dimethylamino-4-phenylcyclohexylmethyl)-4-(1H-indol-3-yl)butyramide hydrochloride, non-polar diastereoisomer 4-(1H-Indol-3-yl)butyric acid (232 mg, 1.0 mmol.), the mixture of the diastereoisomers of (4-aminomethyl-1-phenylcyclohexyl)dimethylamine (203 mg, 1.0 mmol.) and 4-(4,6-dimethoxy-1,3,5-triazin-2-yl)-4-methylmorpholinium chloride (415 mg, 1.5 mmol.) were dissolved in abs. methanol and stirred for 20 h at RT. For working up, the mixture was concentrated and the residue was taken up in water (15 ml), adjusted to pH 11 with 5M NaOH and extracted with EE (4×20 ml). The organic phase was washed with 1M NaOH (3 ml), dried, filtered and concentrated. The residue was a mixture of the bases of the diastereoisomeric target products, which were separated by flash chromatography on silica gel (45 g) (eluant: 700 ml methanol/EE 3:1). The non-polar diastereoisomer was obtained in a yield of 163 mg (0.39 mmol.) and was dissolved in 2-butanone/ethanol (7 ml/2 ml); isopropanolic 5M HCl (125 μl, 0.62 mmol.) was added and stirring was carried out for 2 h at RT. Concentration and drying in vacuo yielded the hydrochloride of the non-polar diastereoisomer of N-(4-dimethylamino-4-phenylcyclohexylmethyl)-2-(1H-indol-3-yl)butyramide in the form of a slightly hygroscopic white solid (177 mg, m.p. 95–100° C.).

Example 8

N-(4-Dimethylamino-4-phenylcyclohexylmethyl)-4-(1H-indol-3-yl)butyramide hydrochloride, polar diastereoisomer In the manner described in Example 7, 154 mg of the polar diastereoisomer of N-(4-dimethylamino-4-phenylcyclohexylmethyl)-2-(1H-indol-3-yl)butyramide were also obtained. These 154 mg were dissolved in 2-butanone/ethanol (7 ml/3 ml), isopropanolic 5M HCl (118 μl, 0.59 mmol.) was added and stirring was carried out for 2 h at RT. Concentration and drying in vacuo yielded 164 mg of the corresponding hydrochloride (slightly hygroscopic, white solid, m.p. 125–132° C.).

Example 9

N-(4-Dimethylamino-4-phenylcyclohexylmethyl)-2-(1H-indol-3-yl)propionamide hydrochloride, non-polar diastereoisomer The non-polar diastereoisomer of (4-aminomethyl-1-phenylcyclohexyl)dimethylamine (232 mg, 1.0 mmol.) and 4-(4,6-dimethoxy-1,3,5-triazin-2-yl)-4-methylmorpholinium chloride (415 mg, 1.5 mmol.) were added to a solution of 3-(1H-indol-3-yl)propionic acid (189 mg, 1.0 mmol.) in abs. methanol, and stirring was carried out for 20 h at RT. For working up, the mixture was concentrated, the residue was taken up in water (10 ml) and ether (10 ml), and the phases were separated. The aqueous phase was adjusted to pH 11 with 5M NaOH and extracted with EE (4×10 ml). The combined organic extracts were washed with 1M NaOH (2×3 ml), dried, filtered and concentrated. For the preparation of the hydrochloride, the resulting non-polar diastereoisomer of N-(4-dimethylamino-4-phenylcyclohexylmethyl)-2-(1H-indol-3-yl)propionamide (220 mg, 0.54 mmol.) was dissolved in 2-butanone; chlorotrimethylsilane (104 µl, 0.82 mmol.) was added thereto, and stirring was carried out for 1 h at RT. After 1 h at 4° C., the resulting precipitate was filtered off with suction, washed with cold 2-butanone (1 ml) and cold ether (2×1 ml) and dried in vacuo. The target compound was obtained in a yield of 168 mg (colourless solid, m.p. 163–168° C. with decomposition).

Example 10

5-(1H-Indol-3-yl)pentanoic acid (4-dimethylamino-4-phenylcyclohexylmethyl)amide hydrochloride, non-polar diastereoisomer In a water separator, indole (50 g, 0.43 mol.), δ-valerolactone (tetrahydropyran-2-one, 49.2 g, 0.49 mol.), potassium hydroxide (35.9 g, 0.64 mol.) in p-cymene (1-isopropyl-4-methylbenzene, 250 ml) were heated at boiling for 4 d, with stirring. For working up, water (200 ml) was added to the mixture, the phases were separated, and the aqueous phase was adjusted to pH 4 with 2M HCl and stored for 2 d at 4° C. in a refrigerator. The resulting solid was filtered off with suction and washed with water (3×20 ml). Recrystallisation from ether (50 ml) yielded 5-(1H-indol-3-yl)pentanoic acid in the form of a white solid having a melting point of 80–83° C. in a yield of 38.8 g.

A mixture of the diastereoisomeric 4-dimethylamino-4-phenylcyclohexanecarbaldehydes (5.06 g, 21.86 mmol.) and hydroxylamine hydrochloride (2.3 g, 33 mmol.) was dissolved in abs. ethanol (150 ml); basic ion exchanger Amberlyst A 21 (15 g, 61.6 mval) was added to the solution, and stirring was carried out at RT. The progress of the reaction was monitored by TLC; when the aldehyde was completely converted, the ion exchanger was filtered off and washing was carried out with ethanol (3×50 ml). The filtrate was concentrated, water (30 ml) was added to the residue, the pH was adjusted to 11 with NaOH (5 mol./l) and extraction was carried out with EE (5×30 ml). The combined extracts were dried, filtered and concentrated. 4-Dimethylamino-4-phenylcyclohexanecarbaldehyde oxime was thus obtained as an isomeric mixture in the form of a yellow oil in a yield of 5.09 g.

Abs. THF (130 ml) was placed in a reaction vessel, under argon, lithium aluminium hydride (1.56 g, 41.2 mmol.) was added, the mixture was heated to 60° C., the isomeric mixture of 4-dimethylamino-4-phenylcyclohexanecarbaldehyde oxime (5.00 g, 20.6 mmol.), dissolved in THF (50 ml), was added dropwise and stirring was carried out at an internal temperature of 60° C. for 12 h. For working up, the mixture was cooled with ice-water; water (70 ml) was added carefully, the resulting suspension was filtered over Celite, the filtration residue was washed with THF, and the THF was removed from the resulting filtrate using a rotary evaporator. The residue was adjusted to pH 11 with NaOH (5 mol./l) and extracted with EE (6×25 ml). The combined extracts were dried, filtered and concentrated. The residue was the mixture of the diastereoisomeric (4-aminomethyl-1-phenylcyclohexyl)dimethylamines (4.1 g, light-brown oil).

For subsequent reactions, this amine was in most cases used in the form of a mixture. Separation of the diastereoisomers was possible by chromatography on silica gel with MeCN/methanol/1N ammonium chloride solution (9:1:1). In this manner there were isolated from a portion (2.7 g) of the diastereoisomeric mixture the non-polar diastereoisomer of (4-aminomethyl-1-phenylcyclohexyl)dimethylamine (981 mg) in the form of a yellow oil, the polar diastereoisomer (610 mg, wax-like) and a viscous mixed fraction (114 mg).

The non-polar diastereoisomer of (4-aminomethyl-1-phenylcyclohexyl)dimethylamine (232 mg, 1.0 mmol.) and 4-(4,6-dimethoxy-1,3,5-triazin-2-yl)-4-methylmorpholinium chloride (415 mg, 1.5 mmol.) were added to a solution of 5-(1H-indol-3-yl)pentanoic acid (217 mg, 1.0 mmol.) in abs. methanol. Stirring was then carried out for 24 h at RT. For working up, the mixture was concentrated, the residue was suspended in water (10 ml), the pH was adjusted to 11 with 5M NaOH, and extraction was carried out with EE (4×10 ml). The organic phase was washed with 1M NaOH, dried, filtered and concentrated. The residue was purified by flash chromatography on silica gel (50 g) with methanol/EE (1 ml/3.5 l) and the non-polar diastereoisomer of 5-(1H-indol-3-yl)pentanoic acid (4-dimethylamino-4-phenylcyclohexylmethyl)amide (306 mg) was isolated. 190 mg (0.44 mmol.) thereof were dissolved in 2-butanone; chlorotrimethylsilane (84 µl, 0.7 mmol.) was added, and stirring was carried out for 2 h. The solvent was decanted off, and the tacky solid was washed with cold 2-butanone (2×1 ml) and cold ether (3×1.5 ml) and dried in vacuo. The hydrochloride of the non-polar diastereoisomer of 5-(1H-indol-3-yl)pentanoic acid (4-dimethylamino-4-phenylcyclohexylmethyl)amide was obtained in a yield of 184 mg (pale-pink solid, m.p. 120–130° C.).

Example 11

6-(1H-Indol-3-yl)hexanoic acid (4-dimethylamino-4-phenylcyclohexylmethyl)amide hydrochloride, non-polar diastereoisomer In a water separator, indole (50 g, 0.43 mol.), ε-caprolactone (oxepan-2-one, 55.9 g, 0.49 mol.), potassium hydroxide (35.9 g, 0.64 mol.) in p-cymene (1-isopropyl-4-methylbenzene, 250 ml) were heated at boiling for 4 d, with stirring. For working up, water (200 ml) was added to the mixture, the phases were separated, and the aqueous phase was adjusted to pH 4 with 2M HCl and stored for 2 d at 4° C. in a refrigerator. The resulting solid was filtered off with suction and washed with water (3×20 ml). Recrystallisation from ether (50 ml) yielded 6-(1H-indol-3-yl)hexanoic acid in the form of a white solid having a melting point of 124–126° C. in a yield of 16.9 g.

The non-polar diastereoisomer of (4-aminomethyl-1-phenylcyclohexyl)dimethylamine (232 mg, 1.0 mmol.) and 4-(4,6-dimethoxy-1,3,5-triazin-2-yl)-4-methylmorpholinium chloride (415 mg, 1.5 mmol.) were added to a solution of 6-(1H-indol-3-yl)hexanoic acid (231 mg, 1.0 mmol.) in abs. methanol, and stirring was carried out for 24 h at RT. For working up, the mixture was concentrated and the residue was suspended in water (10 ml), adjusted to pH 11 with 5M NaOH and extracted with EE (4×10 ml). The combined organic extracts were washed with 1M NaOH (2×2 ml), dried, filtered and concentrated. The residue was purified by flash chromatography on silica gel (50 g) with methanol/EE (1:3, 440 ml) and the non-polar diastereoisomer of 6-(1H-indol-3-yl)hexanoic acid (4-dimethylamino-4-phenylcyclohexylmethyl)amide (266 mg) was isolated in the form of a crystalline solid. 265 mg (6 mmol.) thereof were dissolved in 2-butanone, and chlorotrimethylsilane (113 μl, 0.9 mmol.) was added thereto. A colourless, tacky precipitate immediately formed and was converted into a fine pale-pink solid by the addition of ether. The solid was filtered off, washed with cold ether (3×2 ml) and dried in vacuo. The hydrochloride of 6-(1H-indol-3-yl)hexanoic acid (4-dimethylamino-4-phenylcyclohexylmethyl)amide was thus obtained in a yield of 274 mg (pale-pink solid, m.p. 120–125° C.).

Example 12

N-(4-Dimethylamino-4-phenylcyclohexylmethyl)-2-(1H-indol-3-yl)acetamide hydrochloride, non-polar diastereoisomer The non-polar diastereoisomer of (4-aminomethyl-1-phenylcyclohexyl)dimethylamine (239 mg, 1.03 mmol.) and 4-(4,6-dimethoxy-1,3,5-triazin-2-yl)-4-methylmorpholinium chloride (428 mg, 1.6 mmol.) were added to a solution of 2-(1H-indol-3-yl)acetic acid (180 mg, 1.03 mmol.) in abs. methanol, and stirring was carried out for 24 h at RT. For working up, the mixture was concentrated and the residue was suspended in water (20 ml); 2M HCl (1.5 ml, pH 3) was added, with stirring, and washing was carried out with ether (3×5 ml). The aqueous phase was adjusted to pH 11 with 5M NaOH and extracted with EE (4×10 ml). The organic phase was washed with 1M NaOH (3 ml), dried, filtered and concentrated. The residue was the non-polar diastereoisomer of N-(4-dimethylamino-4-phenylcyclohexylmethyl)-2-(1H-indol-3-yl)acetamide, which was obtained in the form of a solid in a yield of 395 mg (98%). These 395 mg (1.01 mmol.) were dissolved in 2-butanone (5 ml) and acetone (3 ml), and chlorotrimethylsilane (193 μl, 1.52 mmol.) was added thereto. There immediately formed a colourless precipitate, which turned slightly beige in colour at RT. The precipitate was filtered off, washed with cold 2-butanone (2×1 ml) and cold ether (2×2 ml) and dried in vacuo. The hydrochloride of N-(4-dimethylamino-4-phenylcyclohexylmethyl)-2-(1H-indol-3-yl)acetamide was obtained in a yield of 341 mg (light-beige solid, m.p. 128–135° C.).

Example 13

5-(5-Fluoro-1H-indol-3-yl)pentanoic acid (4-dimethylamino-4-phenylcyclohexylmethyl)amide citrate, non-polar diastereoisomer In a water separator, 5-fluoroindole (5.0 g, 37 mmol.), δ-valerolactone (3.83 ml, 42 mmol.), potassium hydroxide (3.09 g, 55 mmol.) in p-cymene (120 ml) were heated to boiling, with stirring. The water separation was stopped after 80 h. For working up, water (50 ml) was added to the mixture at RT and stirring was carried out for 30 min. The phases were then separated in a separating funnel. The aqueous phase was washed with ether (3×20 ml), adjusted to pH 1 with 2M HCl and extracted with ether (5×25 ml). The combined extracts were washed with water (5×10 ml), dried, filtered and concentrated. The residue was purified by flash chromatography on silica gel (375 g) (eluant: 2700 ml of cyclohexane/EE 4:1 followed by 1500 ml of cyclohexane/EE 1:1 and 650 ml of EE). 1.9 g of 5-(5-fluoro-1H-indol-3-yl)pentanoic acid were obtained (beige solid, m.p. 86–92° C.).

A mixture of the diastereoisomers of (4-aminomethyl-1-phenylcyclohexyl)dimethylamine (465 mg, 2.0 mmol.) and 4-(4,6-dimethoxy-1,3,5-triazin-2-yl)-4-methylmorpholinium chloride (830 mg, 3 mmol.) was added to a solution of 5-(5-fluoroindol-3-yl)pentanoic acid (471 mg, 2.0 mmol.) in abs. methanol, and stirring was carried out for 2 d at RT. For working up, the mixture was concentrated, water (10 ml) and 2M HCl (15 ml) were added to the residue, and washing was carried out with ether (25 ml). The aqueous phase was adjusted to pH 11 with 5M NaOH and extracted with EE (4×15 ml). The combined extracts were washed with 1M NaOH, dried, filtered and concentrated. The residue was a diastereoisomeric mixture of the bases of the target product, which was separated by flash chromatography on silica gel (50 g) and purified (eluant: 350 ml of methanol/EE 1:1 followed by 500 ml of methanol/EE 2:1). The non-polar diastereoisomer of 5-(5-fluoro-1H-indol-3-yl)pentanoic acid (4-dimethylamino-4-phenylcyclohexylmethyl)amide (245 mg, 0.55 mmol.) was dissolved in abs. ethanol and added dropwise at RT, with stirring, to citric acid (105 mg, 0.55 mmol.) dissolved in hot ethanol. After stirring for 1 h at RT, the mixture was concentrated to dryness. The citrate of the non-polar diastereoisomer of 5-(5-fluoro-1H-indol-3-yl)pentanoic acid (4-dimethylamino-4-phenylcyclohexylmethyl)amide was obtained (350 mg of light-yellow solid, m.p. 88–92° C.).

Example 14

5-(5-Fluoro-1H-indol-3-yl)pentanoic acid (4-dimethylamino-4-phenylcyclohexylmethyl)amide citrate, polar diastereoisomer In the manner described for Example 13, 266 mg (0.25 mmol.) of the polar diastereoisomer were also obtained and were dissolved in ethanol (10 ml) and added at RT, with stirring, to citric acid (114 mg, 0.59 mmol.) dissolved in hot ethanol (1 ml). After stirring for 1 h at RT, the mixture was concentrated. The citrate of the polar diastereoisomer of 5-(5-fluoro-1H-indol-3-yl)pentanoic acid (4-dimethylamino-4-phenylcyclohexylmethyl)amide was obtained (380 mg of light-yellow solid, m.p. 75–82° C.).

Example 15

N-(4-Dimethylamino-4-phenylcyclohexylmethyl)-2-indol-1-yl-acetamide, non-polar diastereoisomer NaH (0.6 g, 15.0 mmol.) was added, while cooling with ice, to a solution of indole (1.17 g, 10.0 mmol.) and bromoacetic acid methyl ester (1.43 ml, 15 mmol.) in DMF (20 ml), and stirring was carried out for 24 h at RT. For working up, water (50 ml) was added to the mixture, and extraction was carried out with EE (5×20 ml). The combined extracts were dried, filtered and concentrated. Chromatography with EE/cyclohexane (1:7) yielded 1.17 g of indol-1-yl-acetic acid methyl ester in the form of a colourless oil. These 1.17 g (6.18 mmol.) were dissolved in abs. methanol (100 ml); KOH (382 mg, 6.8 mmol.) was added and the mixture was heated at reflux for 2 h. For working up, the mixture was concentrated, water (20 ml) was added to the residue, the pH was adjusted to 4 with 1M HCl and the resulting solid was filtered off with suction. Indol-1-ylacetic acid was obtained in a yield of 0.96 g (white solid, m.p. 128–130° C.).

A mixture of the diastereoisomers of (4-aminomethyl-1-phenylcyclohexyl)dimethylamine (465 mg, 2.0 mmol.) and 4-(4,6-dimethoxy-1,3,5-triazin-2-yl)-4-methylmorpholinium chloride (830 mg, 3 mmol.) was added to a solution of indol-1-ylacetic acid (350 mg, 2.0 mmol.) in abs. methanol (25 ml), and the reaction mixture was stirred for 2 d at RT. For working up, the mixture was concentrated, water (15 ml) was added to the residue, the pH was adjusted to 11 with 5M NaOH and extraction was carried out with EE (3×15 ml). The combined extracts were dried, filtered and concentrated. The residue was a diastereoisomeric mixture of bases of the target products, which was separated by flash chromatography on silica gel (70 g) and purified (eluant: methanol/EE 500 ml 1:3, then 1000 ml 1:1). 244 mg of the non-polar diastereoisomer of N-(4-dimethylamino-4-phenylcyclohexylmethyl)-2-indol-1-yl-acetamide were obtained in the form of a viscous oil. 50 mg (0.128 mmol.) thereof were dissolved in 2-butanone (2 ml), and chlorotrimethylsilane (24.4 μl, 0.193 mmol.) was added thereto. There immediately formed a pale precipitate, which turned a strong colour within a few minutes. The solid was filtered off with suction, washed with ether (3×0.5 ml) and dried in vacuo. The hydrochloride 7/8 of the non-polar target product was thus obtained in a yield of 52 mg (brick-red solid, m.p. 176–186° C.).

Example 16

N-(4-Dimethylamino-4-phenylcyclohexylmethyl)-2-indol-1-yl-acetamide, polar diastereoisomer In the manner described for Example 15, 298 mg of the polar diastereoisomer were also obtained (m.p. 160–163° C.). 289 mg (0.74 mmol.) thereof were dissolved in 2-butanone (6 ml), and chlorotrimethylsilane (141 μl, 1.11 mmol.) was added thereto. There immediately formed a white, voluminous precipitate, which turned pink in colour during the stirring time (RT, 1 h). The solid was filtered off with suction, washed with cold 2-butanone (1×2 ml) and ether (3×2 ml) and dried in vacuo. The hydrochloride of the polar diastereoisomer of N-(4-dimethylamino-4-phenylcyclohexylmethyl)-2-indol-1-yl-acetamide was thus obtained in a yield of 300 mg (pink-coloured solid, m.p. 188–192° C.).

Example 17

6-(5-Fluoro-1H-indol-3-yl)hexanoic acid (4-dimethylamino-4-phenylcyclohexylmethyl)amide citrate, polar diastereoisomer A mixture of the diastereoisomers of (4-aminomethyl-1-phenylcyclohexyl)dimethylamine (347 mg, 1.49 mmol.) and 4-(4,6-dimethoxy-1,3,5-triazin-2-yl)-4-methylmorpholinium chloride (620 mg, 2.2 mmol.) was added to a solution of the potassium salt of 6-(5-fluoro-1H-indol-3-yl)hexanoic acid (430 mg, 1.49 mmol.) in abs. methanol (30 ml), and stirring was carried out for 3 d at RT. For working up, the mixture was concentrated, water (10 ml) and 2M HCl (15 ml) were added to the residue, and washing was carried out with ether (25 ml). The diethyl ether phase was separated off. The aqueous phase and oily drops contained therein were adjusted to pH 11 with 5M NaOH and extracted with EE (4×15 ml). The combined EE extracts were washed with 1M NaOH (2×2 ml), dried, filtered and concentrated. The residue was a diastereoisomeric mixture of the bases of the target product, which was separated by flash chromatography on silica gel (75 g) and purified (eluant: 1500 ml of methanol/EE 1:1). 192 mg of the non-polar diastereoisomer of 6-(5-fluoro-1H-indol-3-yl)hexanoic acid (4-dimethylamino-4-phenylcyclohexylmethyl)amide were obtained (m.p. 52–54° C.).

178 mg (0.38 mmol.) thereof were dissolved in abs. ethanol (4 ml) and added dropwise at RT, with stirring, to citric acid (73.6 mg, 0.38 mmol.) dissolved in hot ethanol (1 ml). After stirring for 2 h at RT, the mixture was concentrated to dryness and dried in vacuo. 250 mg of the citrate of the non-polar diastereoisomer of 6-(5-fluoro-1H-indol-3-yl)hexanoic acid (4-dimethylamino-4-phenylcyclohexylmethyl)amide were obtained in the form of a highly hygroscopic white solid.

Example 18

6-(5-Fluoro-1H-indol-3-yl)hexanoic acid (4-dimethylamino-4-phenylcyclohexylmethyl)amide citrate, polar diastereoisomer In the manner described for Example 17, 262 mg of the polar diastereoisomer of 6-(5-fluoro-1H-indol-3-yl)hexanoic acid (4-dimethylamino-4-phenylcyclohexylmethyl)amide were also obtained (beige solid, m.p. 60–64° C.). 247 mg (0.53 mmol.) thereof were dissolved in abs. ethanol (4 ml) and added dropwise at RT, with stirring, to citric acid (102 mg, 0.53 mmol.) dissolved in hot ethanol (1 ml). After stirring for 2 h at RT, the mixture was concentrated to dryness and dried in vacuo. 348 mg of the corresponding citrate were obtained in the form of a slightly hygroscopic white solid.

Example 19

N-(4-Dimethylamino-4-phenylcyclohexylmethyl)-3-indol-1-ylpropionamide citrate, non-polar diastereoisomer KOH (11.5 g, 0.2 mol.) was added to a solution of indole (5.0 g, 40.0 mmol.) and 3-bromopropionic acid methyl ester (4.37 ml, 40 mmol.) in DMSO (35 ml), and stirring was carried out for 24 h at RT. For working up, water (50 ml) was added to the mixture, washing was carried out with ether (5×20 ml), and the aqueous phase was adjusted to pH 4 with 1M HCl and extracted with ether (5×20 ml). The combined extracts were dried, filtered and concentrated. Chromatography with methanol yielded 3-indol-1-ylpropionic acid in a yield of 3.8 g (white solid, m.p. 54–56° C.).

A mixture of the diastereoisomers of (4-aminomethyl-1-phenylcyclohexyl)dimethylamine (465 mg, 2.0 mmol.) and 4-(4,6-dimethoxy-1,3,5-triazin-2-yl)-4-methylmorpholinium chloride (830 mg, 3 mmol.) was added to a solution of 3-indol-1-ylpropionic acid (383 mg, 2.0 mmol.) in abs. methanol (35 ml), and stirring was carried out for 2 d at RT.

For working up, the mixture was concentrated, water (15 ml) was added to the residue, the pH was adjusted to 11 with 5M NaOH and extraction was carried out with EE (4×15 ml). The combined extracts were dried, filtered and concentrated. A mixture of the diastereoisomeric bases of the target product was obtained as the residue and was separated by flash chromatography on silica gel (70 g) and purified (eluant: 1300 ml of methanol/EE 1:1). 254 mg of the non-polar diastereoisomer of N-(4-dimethylamino-4-phenylcyclohexylmethyl)-3-indol-1-ylpropionamide were obtained in the form of a viscous oil. 226 mg (0.56 mmol.) thereof were dissolved in abs. ethanol (3 ml) and added dropwise at RT, with stirring, to citric acid (108 mg, 0.56 mmol.) dissolved in hot ethanol (1 ml). After stirring for 1 h at RT, the white precipitate that had formed was filtered off with suction, washed with cold ethanol (1 ml) and with diethyl ether (3×1 ml) and dried in vacuo. 262 mg of the corresponding citrate were obtained (light-beige solid, m.p. 192–194° C.).

Example 20

N-(4-Dimethylamino-4-phenylcyclohexylmethyl)-3-indol-1-ylpropionamide citrate, polar diastereoisomer In the manner described for Example 19, 236 mg of the polar diastereoisomer of N-(4-dimethylamino-4-phenylcyclohexylmethyl)-3-indol-1-ylpropionamide were also obtained (m.p. 160–163° C.). 223 mg (0.55 mmol.) thereof were dissolved in abs. ethanol (5 ml) and added dropwise at RT, with stirring, to citric acid (106 mg, 0.55 mmol.) dissolved in hot ethanol (1 ml). After stirring for 1 h at RT, the reaction solution was reduced to 0.5 ml in vacuo; ether (15 ml) was added, followed by vigorous stirring for 1 h at RT and concentration to dryness. 328 mg of the corresponding citrate were obtained (light-yellow foam, m.p. 85–89° C.).

Example 21

4-(5-Fluoro-1H-indol-3-yl)butanoic acid (4-dimethylamino-4-phenylcyclohexylmethyl)amide hydrochloride, non-polar diastereoisomer A mixture of the diastereoisomers of (4-aminomethyl-1-phenylcyclohexyl)dimethylamine (465 mg, 2 mmol.) and 4-(4,6-dimethoxy-1,3,5-triazin-2-yl)-4-methylmorpholinium chloride (830 mg, 3 mmol.) was added to a solution of 4-(5-fluoro-1H-indol-3-yl)butanoic acid (443 mg, 2 mmol.) in abs. methanol (10 ml), and stirring was carried out for 24 h at RT. For working up, the mixture was concentrated, water (5 ml) was added to the solid residue, and the pH was adjusted to 11 with 2M NaOH. Extraction was carried out with EE (5×10 ml), and the combined extracts were washed with 1M NaOH (2×3 ml), dried, filtered and concentrated. The residue was a diastereoisomeric mixture of the bases of the target product, which was separated by flash chromatography on silica gel (50 g) and purified (eluant: 700 ml of ethanol/EE 1:1). 260 mg (0.59 mmol.) of the non-polar diastereoisomer of 4-(5-fluoro-1H-indol-3-yl) butanoic acid (4-dimethylamino-4-phenylcyclohexylmethyl)amide were obtained in the form of a light-yellow viscous oil; the oil was dissolved in 2-butanone (7 ml) and chlorotrimethylsilane (113 µl, 0.89 mmol.) was added thereto. There immediately formed a white precipitate, which was deposited in a tacky manner on the wall of the flask. The solvent was reduced to about 3 ml in vacuo and, after addition of ether (3 ml), vigorous stirring was carried out at RT for 1 h. The solid that formed was filtered off with suction, washed with ether (3×1.5 ml) and dried in vacuo. The hydrochloride of the non-polar diastereoisomer of 4-(5-fluoro-1H-indol-3-yl)butanoic acid (4-dimethylamino-4-phenylcyclohexylmethyl)amide was thus obtained in the form of a hygroscopic solid in a yield of 272 mg.

Example 22

4-(5-Fluoro-1H-indol-3-yl)butanoic acid (4-dimethylamino-4-phenylcyclohexylmethyl)amide hydrochloride, polar diastereoisomer In the manner described for Example 21, 240 mg (0.55 mmol.) of the polar diastereoisomer of 4-(5-fluoro-1H-indol-3-yl)butanoic acid (4-dimethylamino-4-phenylcyclohexylmethyl)amide were also obtained (m.p. 160–163° C.) and were dissolved in 2-butanone (7 ml); chlorotrimethylsilane (105 µl, 0.83 mmol.) was added thereto. There immediately formed a pale precipitate, which was deposited in a tacky manner on the wall of the flask. The solvent was reduced to about 3 ml in vacuo and, after addition of ether (3 ml), vigorous stirring was carried out for 1 h at RT. The solid that formed was filtered off with suction, washed with ether (3×1.5 ml) and dried in vacuo. The hydrochloride of the polar diastereoisomer of 4-(5-fluoro-1H-indol-3-yl)butanoic acid (4-dimethylamino-4-phenylcyclohexylmethyl) amide was thus obtained in the form of a hygroscopic solid in a yield of 234 mg.

Example 23

6-(5-Chloro-1H-indol-3-yl)hexanoic acid (4-dimethylamino-4-phenylcyclohexylmethyl)amide hydrochloride, non-polar diastereoisomer A mixture of the diastereoisomers of (4-aminomethyl-1-phenylcyclohexyl)dimethylamine (152 mg, 0.65 mmol.) and 4-(4,6-dimethoxy-1,3,5-triazin-2-yl)-4-methylmorpholinium chloride (207.5 mg, 0.75 mmol.) was added to a solution of 6-(5-chloro-1H-indol-3-yl)hexanoic acid (174 mg, 0.65 mmol.) in abs. methanol (5 ml), and stirring was carried out for 2 d at RT. For working up, the mixture was concentrated, water (15 ml) was added to the residue, the pH was adjusted to 11 with 5M NaOH and extraction was carried out with EE (4×15 ml). The combined extracts were washed with 1M NaOH (2×2 ml), dried, filtered and concentrated. The residue was a diastereoisomeric mixture of the bases of the target product, which was separated by flash chromatography on silica gel (35 g) and purified (eluant: 600 ml of methanol/EE 1:1). The resulting non-polar diastereoisomer (110 mg, 0.23 mmol.) was dissolved in 2-butanone (5 ml), and chlorotrimethylsilane (44 µl, 0.35 mmol.) was added thereto. There immediately formed a white precipitate, which after 15 min. was deposited in a tacky manner on the wall of the flask. The solvent was reduced to about 0.5 ml in vacuo, ether (2 ml) was added to the residue, and vigorous stirring was carried out for 1 h. The solid that formed was filtered off with suction, washed with ether (2×1 ml) and dried in vacuo. The hydrochloride of the non-polar diastereoisomer of 6-(5-chloro-1H-indol-3-yl)hexanoic acid (4-dimethylamino-4-phenylcyclohexylmethyl)amide was thus obtained in the form of a slightly hygroscopic solid in a yield of 124 mg (m.p. 135–145° C.).

Example 24

6-(5-Chloro-1H-indol-3-yl)hexanoic acid (4-dimethylamino-4-phenylcyclohexylmethyl)amide hydrochloride, polar diastereoisomer In the manner described for Example 23, 97 mg (0.20 mmol.) of the polar diastereoisomer of 6-(5-chloro-1H-indol-3-yl)hexanoic acid (4-dimethylamino-4-phenylcyclohexylmethyl)amide were also obtained and were dissolved in 2-butanone (5 ml); chlorotrimethylsilane (38 μl, 0.30 mmol.) was added thereto. There immediately formed a white precipitate, which was deposited in a tacky manner on the wall of the flask. The solvent was reduced to about 0.5 ml in vacuo, ether (2 ml) was added to the residue, and vigorous stirring was carried out for 1 h. The solid that formed was filtered off with suction, washed with ether (2×1 ml) and dried in vacuo. The hydrochloride of the polar diastereoisomer of 6-(5-chloro-1H-indol-3-yl)hexanoic acid (4-dimethylamino-4-phenylcyclohexylmethyl)amide was thus obtained in the form of a slightly hygroscopic solid in a yield of 109 mg (m.p. 110–125° C.).

Example 25

N-(4-Dimethylamino-4-phenylcyclohexyl)-2-(5-fluoro-2-methyl-1H-indol-3-yl)acetamide citrate, non-polar diastereoisomer 4-Oxo-pentanoic acid ethyl ester (17.6 ml, 0.124 mol.) and conc. sulfuric acid (10 ml) were added to a solution of 4-fluorophenylhydrazine (20.2 g, 0.124 mol.) in abs. ethanol (90 ml), and the mixture was heated at reflux for 4 h. For working up, the mixture was filtered over silica gel and washed with ethanol (3×20 ml). The solution was poured into 500 ml of ice-water and extracted with ether (3×100 ml). The combined extracts were washed with 2M sodium hydrogen carbonate solution (50 ml), dried, filtered and concentrated. By recrystallisation from EE/cyclohexane (1:1) it was possible to obtain (5-fluoro-2-methyl-1H-indol-3-yl)acetic acid ethyl ester in a yield of 4.5 g (yellow solid, m.p. 61–62° C.).

This ester (4.5 g, 0.019 mol.) was added to a solution of KOH (2.13 g, 38 mmol.) in methanol (100 ml), and the mixture was heated at reflux for 30 min. For working up, the mixture was diluted with water (100 ml) and methanol was distilled off using a rotary evaporator. The aqueous phase was adjusted to pH 4 with 2M HCl and stored for 2 h at 4° C. The white solid that precipitated was filtered off with suction and washed with methanol. (5-Fluoro-2-methyl-1H-indol-3-yl)acetic acid was obtained in a yield of 3.25 g (m.p. 136–138° C.).

A mixture of the diastereoisomers of (4-aminomethyl-1-phenylcyclohexyl)dimethylamine (465 mg, 2 mmol.) and 4-(4,6-dimethoxy-1,3,5-triazin-2-yl)-4-methylmorpholinium chloride (830 mg, 3 mmol.) was added to a solution of 2-(5-fluoro-2-methyl-1H-indol-3-yl)acetic acid (414 mg, 2 mmol.) in abs. methanol (16 ml), and stirring was carried out for 24 h at RT. For working up, the mixture was concentrated, water (15 ml) was added to the solid residue, the pH was adjusted to 11 with 5M NaOH, and extraction was carried out with EE (5×15 ml). The combined extracts were washed with 1M NaOH (2×3 ml), dried, filtered and concentrated. The residue was a mixture of the diastereoisomeric bases of the target product, which was separated by flash chromatography on silica gel (80 g) and purified (eluant: 1200 ml of methanol/EE 1:1). The non-polar diastereoisomer (345 mg, 0.82 mmol., light-yellow solid, m.p. 75–80° C.) was dissolved in abs. ethanol (5 ml) and added dropwise at RT, with stirring, to citric acid (157 mg, 0.82 mmol.) dissolved in hot ethanol (1 ml). After stirring for 1 h at RT, the mixture was concentrated and dried in vacuo. 501 mg of the citrate of the non-polar diastereoisomer of N-(4-dimethylamino-4-phenylcyclohexyl)-2-(5-fluoro-2-methyl-1H-indol-3-yl)acetamide were obtained (cream-coloured foam, m.p. 95–108° C.).

Example 26

N-(4-Dimethylamino-4-phenylcyclohexyl)-2-(5-fluoro-2-methyl-1H-indol-3-yl)acetamide citrate, polar diastereoisomer In the manner described for Example 25, 332 mg of the polar diastereoisomer of N-(4-dimethylamino-4-phenylcyclohexyl)-2-(5-fluoro-2-methyl-1H-indol-3-yl)acetamide were also obtained (light-yellow solid, m.p. 80–86° C.). 326 mg (0.77 mmol.) thereof were dissolved in abs. ethanol (5 ml) and added dropwise at RT, with stirring, to citric acid (149 mg, 0.77 mmol.) dissolved in hot ethanol (1 ml). After stirring for 2 h at RT, the mixture was concentrated and dried in vacuo. 470 mg of the corresponding citrate were obtained in the form of a cream-coloured foam (m.p. 98–105° C.).

Example 27

1-(4-Dimethylamino-4-phenylcyclohexylmethyl)-3-(3-phenylpropyl)urea hydrochloride, non-polar diastereoisomer Chloroformic acid phenyl ester (3.29 g, 21.0 mmol.) and pyridine (1.74 g, 22.0 mmol.) were added to a solution of 3-phenylpropylamine (2.7 g, 20.0 mmol.) in abs. DCM (50 ml), and stirring was carried out for 24 h at RT. For working up, the mixture was washed in succession with water (2×20 ml), 1M HCl (2×20 ml) and 1N NaOH (2×20 ml) and then the organic phase was dried, filtered and concentrated. (3-Phenylpropyl)carbamic acid phenyl ester was obtained in a yield of 4.11 g by recrystallisation from EE/hexane (1:1) (white solid, m.p. 55–56° C.).

A mixture of the diastereoisomers of (4-aminomethyl-1-phenylcyclohexyl)dimethylamine (466 mg, 2.0 mmol.) was added to a solution of (3-phenylpropyl)carbamic acid phenyl ester (511 mg, 2.0 mmol.) in dioxane (15 ml), and heating was carried out for 12 h at reflux. For working up, the mixture was concentrated, water (10 ml) was added to the residue, the pH was adjusted to 11 with 5M NaOH, and extraction was carried out with EE (3×20 ml). The combined extracts were washed with 1M NaOH (1×5 ml), dried, filtered and concentrated. The residue was a diastereoisomeric mixture of the target products, which was separated by flash chromatography on silica gel (60 g) and purified (eluant: 1000 ml of ethanol/EE 1:1). The non-polar urea (310 mg, 0.79 mmol., yellow oil) was dissolved in acetone (5 ml) and 2-butanone (15 ml), and chlorotrimethylsilane (150 μl, 1.2 mmol.) was added dropwise at RT, with stirring. After stirring for 1 h, the reaction solution was reduced to about 1 ml in vacuo, ether (10 ml) was added thereto, and vigorous stirring was carried out for 1 h at RT. The solid that formed was filtered off with suction, washed with ether (3×3 ml) and dried in vacuo. 339 mg of the hydrochloride of the non-polar diastereoisomer of 1-(4-dimethylamino-4-phenylcyclohexylmethyl)-3-(3-phenylpropyl)urea were obtained (white solid, m.p. 85–95° C.).

Example 28

1-(4-Dimethylamino-4-phenylcyclohexylmethyl)-3-(3-phenylpropyl)urea hydrochloride, polar diastereoisomer In the manner described for Example 27, 255 mg of the polar diastereoisomer of 1-(4-dimethylamino-4-phenylcyclohexylmethyl)-3-(3-phenylpropyl)urea were also obtained (m.p. 159–165° C.). 249 mg (0.63 mmol.) thereof were dissolved in acetone (7 ml) and 2-butanone (15 ml), and chlorotrimethylsilane (121 µl, 0.95 mmol.) was added dropwise at RT, with stirring. After stirring for 1 h, the reaction solution was reduced to about 0.5 ml in vacuo, ether (10 ml) was added thereto, and vigorous stirring was carried out for 1 h at RT. The resulting solid was filtered off with suction, washed with ether (3×2.5 ml) and dried in vacuo. 270 mg of the corresponding hydrochloride of the polar urea were obtained (greyish-white solid, m.p. 100–110° C.).

Example 29

1-(4-Dimethylamino-4-phenylcyclohexylmethyl)-3-[2-(1H-indol-3-yl)ethyl]urea hydrochloride, polar diastereoisomer Chloroformic acid phenyl ester (3.29 g, 21.0 mmol.) and pyridine (1.74 g, 22.0 mmol.) were added to a solution of tryptamine (2-(1H-indol-3-yl)ethylamine, 3.2 g, 20.0 mmol.) in abs. DCM (50 ml), and stirring was carried out for 24 h at RT. For working up, the mixture was washed with water (2×20 ml), 1M HCl (2×20 ml) and 1M NaOH (2×20 ml), and the organic phase was dried, filtered and concentrated. [2-(1H-Indol-3-yl)ethyl]carbamic acid phenyl ester was obtained in a yield of 5.58 g (white solid, m.p. 44–46° C.).

A mixture of the diastereoisomers of (4-aminomethyl-1-phenylcyclohexyl)dimethylamine (465 mg, 2.0 mmol.) was added to a solution of [2-(1H-indol-3-yl)ethyl]carbamic acid phenyl ester (561 mg, 2.0 mmol.) in dioxane (15 ml), and stirring was carried out for 12 h at reflux. For working up, the mixture was concentrated, water (10 ml) was added to the residue, the pH was adjusted to 11 with 5M NaOH, and extraction was carried out with EE (3×20 ml). A small amount of the base of the polar target product was thereby produced in the form of a solid and was filtered off with suction, washed with ether (2×20 ml) and dried (100 mg, m.p. 204–208° C.). The combined extracts were washed with 1M NaOH (5 ml), dried, filtered and concentrated. The resulting diastereoisomeric mixture of the target products was separated by flash chromatography on silica gel (50 g) and purified (eluant: 1100 ml of ethanol/EE 1:1), a further amount of the base of the polar target product (55 mg, m.p. 202–207° C.) being isolated. 128 mg of this polar diastereoisomer (0.3 mmol.) were dissolved in abs. ethanol (15 ml) and 2-butanone (5 ml), and 5M isopropanolic hydrochloric acid (92 µl, 0.46 mmol.) was added dropwise at RT, with stirring. After stirring for 1 h at RT, the reaction solution was reduced to about 2 ml in vacuo, and ether (10 ml) was added thereto. The tacky precipitate was detached from the vessel wall mechanically, and the suspension was stirred vigorously for 1 h at RT. The precipitate that formed was filtered off with suction, washed with ether (3×1.5 ml) and dried in vacuo. The hydrochloride of the polar diastereoisomer of 1-(4-dimethylamino-4-phenylcyclohexylmethyl)-3-[2-(1H-indol-3-yl)ethyl]urea was thus obtained in the form of a cream-coloured solid in a yield of 137 mg.

Example 30

1-(4-Dimethylamino-4-phenylcyclohexylmethyl)-3-[2-(1H-indol-3-yl)ethyl]urea, non-polar diastereoisomer In the manner described for Example 29, 264 mg of the non-polar diastereoisomer of 1-(4-dimethylamino-4-phenylcyclohexylmethyl)-3-[2-(1H-indol-3-yl)ethyl]urea were also obtained (m.p. 159–163° C.).

Example 31

1-(4-Dimethylamino-4-phenylcyclohexylmethyl)-3-[2-(1H-indol-3-yl)-1-methylethyl]urea hydrochloride, non-polar diasteroisomer Chloroformic acid phenyl ester (760 µl, 6.03 mmol.) and pyridine (510 µl, 6.31 mmol.) were added to a solution of rac. 2-(1H-indol-3-yl)-1-methylethylamine (1.0 g, 5.74 mmol.) in abs. DCM (20 ml), and stirring was carried out for 24 h at RT. For working up, the mixture was washed with water (2×20 ml), with 1M HCl (2×20 ml) and with 1M NaOH (2×20 ml), then dried, filtered and concentrated. [2-(1H-Indol-3-yl)-1-methylethyl]carbamic acid phenyl ester was obtained in the form of a white solid in a yield of 1.35 g.

The non-polar diastereoisomer of (4-aminomethyl-1-phenylcyclohexyl)dimethylamine (163 mg, 0.70 mmol.) was added to a solution of [2-(1H-indol-3-yl)-1-methylethyl]carbamic acid phenyl ester (206 mg, 0.70 mmol.) in dioxane (7 ml), and heating was carried out for 14 h at reflux. For working up, the clear reaction mixture was added to ice-water (15 ml), adjusted to pH 11 with 5M NaOH and extracted with ether (3×20 ml). The combined extracts were dried, filtered and concentrated. The residue was purified by flash chromatography on silica gel (30 g) (eluant: 400 ml of ethanol/EE 1:2). The base of the target product was thus obtained in a yield of 185 mg (white solid, m.p. 89–92° C.).

157 mg (0.36 mmol.) thereof were dissolved in 2-butanone (6 ml), and chlorotrimethylsilane (69 µl, 0.6 mmol.) was added dropwise at RT, with stirring. After stirring for 1 h at RT, ether (25 ml) was added and vigorous stirring was carried out for 1 h at RT. The solid that formed was filtered off with suction, washed with ether (3×2 ml) and dried in vacuo. 163 mg of the hydrochloride of the non-polar diastereoisomer of 1-(4-dimethylamino-4-phenylcyclohexylmethyl)-3-[2-(1H-indol-3-yl)-1-methylethyl]urea were obtained (white solid, m.p. 150–155° C.).

Example 32

1-(4-Dimethylamino-4-phenylcyclohexylmethyl)-3-[2-(1H-indol-3-yl)-1-methylethyl]urea hydrochloride, polar diastereoisomer The polar diastereoisomer of (4-aminomethyl-1-phenylcyclohexyl)dimethylamine (163 mg, 0.70 mmol.) was added to a solution of [2-(1H-indol-3-yl)-1-methylethyl]carbamic acid phenyl ester (206 mg, 0.70 mmol.) in dioxane (7 ml), and heating was carried out for 14 h at reflux. A pale precipitate formed at room temperature. The precipitate was filtered off with suction and washed with cold dioxane (2 ml) and with ether (3×3 ml). The target product was thus obtained in a yield of 231 mg (white solid, m.p. 140–146° C.).

219 mg (0.50 mmol.) thereof were dissolved in 2-butanone (40 ml), and chlorotrimethylsilane (95 μl, 0.75 mmol.) was added dropwise at RT, with stirring. After stirring for 1 h at RT, ether (15 ml) was added and vigorous stirring was carried out for 1 h at RT. The solid that formed was filtered off with suction, washed with ether (3×3 ml) and dried in vacuo. 219 mg of the hydrochloride of the polar diastereoisomer of 1-(4-dimethylamino-4-phenylcyclohexylmethyl)-3-[2-(1H-indol-3-yl)-1-methylethyl]urea were obtained (white solid, m.p. 170–174° C.).

Example 33

1-(4-Dimethylamino-4-phenylcyclohexylmethyl)-3-[2-(5-fluoro-1H-indol-3-yl)ethyl]urea citrate, polar diastereoisomer A mixture of the diastereoisomers of (4-dimethylamino-4-phenylcyclohexylmethyl)carbamic acid phenyl ester (590 mg, 1.67 mmol.) was added to a solution of 5-fluorotryptamine (298 mg, 1.67 mmol.) in dioxane (14 ml), and the reaction mixture was heated for 24 h at reflux. A white precipitate formed at room temperature. The precipitate was filtered off with suction, washed with dioxane (1×1 ml) and with ether (4×2 ml) and then dried. The resulting white solid was the base of the target product (220 mg, m.p. 97–101° C.). 208 mg (0.476 mmol.) thereof were dissolved in abs. ethanol (3.5 ml), and citric acid (93 mg, 0.481 mmol.) was added in a single portion at about 40° C., with stirring. After stirring for 2 h at RT, the reaction mixture was reduced to about 1 ml, and ether (20 ml) was added in portions thereto. The resulting precipitate was filtered off with suction after 1 h, washed with ether (3×3 ml) and dried in vacuo. 230 mg of the citrate of the polar diastereoisomer of 1-(4-dimethylamino-4-phenylcyclohexylmethyl)-3-[2-(5-fluoro-1H-indol-3-yl)ethyl]urea were obtained in the form of a white solid.

Example 34

1-(4-Dimethylamino-4-phenylcyclohexylmethyl)-3-[2-(5-fluoro-1H-indol-3-yl)ethyl]urea citrate, non-polar diastereoisomer The filtrate obtained according to Example 33 after removal of the polar urea by filtration was concentrated using a rotary evaporator, and the residue was purified by flash chromatography on silica gel (60 g) (eluant: 800 ml of methanol/EE 1:1). The non-polar base of the target product was thus obtained in a yield of 187 mg (m.p. 70–73° C.).

187 mg (0.428 mmol.) thereof were dissolved in abs. ethanol (3.5 ml), and citric acid (83 mg, 0.43 mmol.) was added in a single portion at about 40° C., with stirring. After stirring for 2 h at RT, ether (20 ml) was added to the reaction mixture, and stirring was again carried out for 1 h at RT. After 15 min. in a refrigerator, the white precipitate was filtered off with suction, washed with cold ether (3×3 ml) and dried in vacuo. 214 mg of the citrate of the non-polar diastereoisomer of 1-(4-dimethylamino-4-phenylcyclohexylmethyl)-3-[2-(5-fluoro-1H-indol-3-yl)ethyl]urea were obtained in the form of a white solid.

Example 35

4-(5-Fluoro-1H-indol-3-yl)piperidine-1-carboxylic acid (4-dimethylamino-4-phenylcyclohexylmethyl)amide citrate, non-polar diastereoisomer A mixture of the diastereoisomers of (4-dimethylamino-4-phenylcyclohexylmethyl)carbamic acid phenyl ester (388 mg, 1.1 mmol.) was added to a solution of 5-fluoro-3-piperidin-4-yl-1H-indole (240 mg, 1.1 mmol.) in dioxane (11 ml), and the reaction mixture was heated for 16 h at reflux. For working up, the mixture was concentrated and the residue was separated into the diastereoisomers by flash chromatography on silica gel (25 g) and purified (eluant: 900 ml of methanol/EE 1:1). 150 mg (0.314 mmol.) of the non-polar base of the target product (m.p. 95–98° C.) were obtained. The product was dissolved in abs. ethanol (11 ml) and DCM (2 ml), and citric acid (61.1 mg, 0.318 mmol.) was added in a single portion at about 40° C., with stirring. After stirring for 5 h at RT, the suspension was cooled overnight in a refrigerator and after 20 h the precipitate was filtered off with suction, washed with ether (3×3 ml) and dried in vacuo. 117 mg of the citrate of the non-polar diastereoisomer of 4-(5-fluoro-1H-indol-3-yl)piperidine-1-carboxylic acid (4-dimethylamino-4-phenylcyclohexylmethyl)amide were obtained (white solid, m.p. 162–166° C.).

Example 36

4-(5-Fluoro-1H-indol-3-yl)piperidine-1-carboxylic acid (4-dimethylamino-4-phenylcyclohexylmethyl) amide citrate, polar diastereoisomer In the manner described for Example 35, 120 mg (0.252 mmol.) of the polar base of the target product were also obtained (m.p. 206–208° C.). The product was dissolved in abs. ethanol (2 ml), and citric acid (48.9 g, 0.254 mmol.) was added in a single portion at about 40° C., with stirring. The reaction mixture was stirred for 20 h at RT, then concentrated to dryness and dried in vacuo. 168 mg of the citrate of the polar diastereoisomer of 4-(5-fluoro-1H-indol-3-yl) piperidine-1-carboxylic acid (4-dimethylamino-4-phenylcyclohexylmethyl)amide were obtained (cream-coloured solid foam, m.p. 110–115° C.).

Example 37

4-(5-Methoxy-1H-indol-3-yl)-piperidine-1-carboxylic acid (4-dimethylamino-4-phenylcyclohexylmethyl)amide citrate, non-polar diastereoisomer 5-Methoxy-3-piperidin-4-yl-1H-indole (169 mg, 0.735 mmol.) in dioxane (4.5 ml) and a mixture of the diastereoisomers of (4-dimethylamino-4-phenylcyclohexylmethyl) carbamic acid phenyl ester (259 mg, 0.735 mmol.) were dissolved in each of two microwave reaction vessels. The reaction mixtures were heated in the microwave for 52 min. at 150° C. (test 1) and for 2 min. at 200° C. (test 2). For working up, the solvent was removed from both mixtures by distillation in vacuo and the respective residues, combined, were separated into the diastereoisomeric bases of the target product by flash chromatography on silica gel (30 g and 40 g) and purified (eluant: about 600 ml of methanol/EE 1:1). 166 mg (m.p. 106–107° C.) and 89 mg (m.p. 110–112° C.) of the non-polar base of the target product were obtained. 203 mg (0.415 mmol.) thereof were dissolved in abs. ethanol (2 ml) and DCM (3 ml), and citric acid (81 mg, 0.419 mmol.) was added thereto in a single portion at about 40° C., with stirring. A white precipitate immediately formed at RT. After stirring for 2 h at RT, ether (25 ml) was added to the suspension and stirring was carried out overnight. After 20 h, the precipitate was filtered off with suction, washed with ether (3×1 ml) and dried in vacuo. 250 mg of the non-polar diastereoisomer of 4-(5-methoxy-1H-indol-3-yl)-piperidine-1-carboxylic acid (4-dimethylamino-4-phenylcyclohexylmethyl)amide were obtained (white solid, m.p. 155–158° C.).

Example 38

4-(5-Methoxy-1H-indol-3-yl)-piperidine-1-carboxylic acid (4-dimethylamino-4-phenylcyclohexylmethyl)amide citrate, polar diastereoisomer

In the manner described for Example 37, 108 mg (m.p. 98–100° C.) and 92 mg (m.p. 92–97° C.) of the base of the polar diastereoisomer of the target product were also obtained. 197 mg (0.403 mmol.) thereof were dissolved in abs. ethanol (3 ml) and DCM (5 ml), and citric acid (78.3 mg, 0.407 mmol.) were added thereto in a single portion at about 40° C., with stirring. The reaction mixture was stirred for 2 h at RT, the solution was concentrated to 2 ml, and ether (30 ml) was added thereto. The suspension was stirred for 20 h at RT, and the precipitate that formed was filtered off with suction, washed with ether (3×1.5 ml) and dried in vacuo. 239 mg of the polar diastereoisomer of 4-(5-methoxy-1H-indol-3-yl)-piperidine-1-carboxylic acid (4-dimethylamino-4-phenylcyclohexylmethyl)amide were obtained (white solid, m.p. 139–143° C.).

Example 39

1-(4-Dimethylamino-4-phenylcyclohexylmethyl)-3-[2-(1H-indol-3-yl)ethyl]thiourea citrate, non-polar diastereoisomer

2-(1H-Indol-3-yl)ethylamine ("tryptamine", 320 mg, 2 mmol.) was dissolved under argon in abs. chloroform (10 ml), and triethylamine (533 μl, 4 mmol.) was added thereto. Thiophosgene (153 μl, 2 mmol.) was added dropwise to this mixture. After 18 h, (4-aminomethyl-1-phenylcyclohexyl)dimethylamine (465 mg, 2 mmol.), dissolved in chloroform (5 ml), was added, and stirring was carried out for 20 h at RT. For working up, the mixture was washed with saturated NaHCO$_3$ solution (3×5 ml) and water (5 ml), and the organic phase was dried, filtered and concentrated. The resulting crude product was a diastereoisomeric mixture of the bases of the target product, which was separated by column chromatography on silica gel (70 g, eluant: 1500 ml of MeOH/EE 1:1) and purified. 266 mg of the non-polar diastereoisomer were obtained (m.p. 84–87° C.). 253 mg thereof (0.582 mmol.) were dissolved in ethanol (4 ml) at RT, and a solution of citric acid (123 mg, 0.588 mmol.) in ethanol (1 ml) was added. After 2 h, 20 ml of ether were added to the mixture, stirring was carried out for 18 h, and the resulting solid was filtered off with suction, washed with ether (3×2 ml) and dried. The citrate of the non-polar diastereoisomer of 1-(4-dimethylamino-4-phenylcyclohexylmethyl)-3-[2-(1H-indol-3-yl)ethyl]thiourea could thus be obtained in the form of a light-yellow solid in a yield of 297 mg.

Example 40

1-(4-Dimethylamino-4-phenylcyclohexylmethyl)-3-[2-(1H-indol-3-yl)ethyl]thiourea citrate, polar diastereoisomer

In the manner described for Example 39, the polar diastereoisomer of 1-(4-dimethylamino-4-phenylcyclohexylmethyl)-3-[2-(1H-indol-3-yl)ethyl]thiourea was also obtained (274 mg, m.p. 92–95° C.). 262 mg thereof (0.603 mmol.) were converted analogously to Example 39 into 317 mg of the corresponding citrate (beige and hygroscopic solid).

Example 41

2-[3-(4-Dimethylamino-4-phenylcyclohexylmethyl)thioureido]-3-(1H-indol-3-yl)propionic acid methyl ester citrate, non-polar diastereoisomer

2-Amino-3-(1H-indol-3-yl)propionic acid methyl ester hydrochloride ("tryptophan methyl ester hydrochloride", 382 mg, 1.5 mmol.) was dissolved under argon in abs. chloroform (15 ml), and triethylamine (633 μl, 4.5 mmol.) were added thereto. Thiophosgene (115 μl, 1.5 mmol.) dissolved in chloroform (10 ml) was added dropwise to this mixture at −5° C. After 18 h, (4-aminomethyl-1-phenylcyclohexyl)dimethylamine (465 mg, 2 mmol.) dissolved in chloroform (10 ml) was added dropwise at RT, and stirring was carried out for 48 h. For working up, the mixture was washed with saturated NaHCO$_3$ solution (3×5 ml) and water (5 ml), and the organic phase was dried, filtered and concentrated. The resulting crude product was a diastereoisomeric mixture of the bases of the target product, which was separated by column chromatography on silica gel (100 g, eluant: 1500 ml of MeOH/EE 1:4, then 500 ml of MeOH/EE 1:1) and purified. 193 mg of the non-polar diastereoisomer were obtained in the form of a light-yellow solid (m.p. 178–183° C.). 135 mg thereof (0.274 mmol.) were dissolved in hot ethanol (11 ml), and a solution of citric acid (57.9 mg, 0.3 mmol.) in ethanol (1 ml) was added thereto. After 4 h, the mixture was concentrated to 2 ml, and ether (30 ml) was slowly added. The suspension was stirred for 20 h at RT and cooled for 2 h in a refrigerator. The resulting solid was filtered off with suction, washed with cold ether (2×1 ml) and dried. The citrate of the non-polar diastereoisomer of 2-[3-(4-dimethylamino-4-phenylcyclohexylmethyl)thioureido]-3-(1H-indol-3-yl)propionic acid methyl ester could thus be obtained in a yield of 165 mg (yellow solid, m.p. 158–163° C.).

Example 42

2-[3-(4-Dimethylamino-4-phenylcyclohexylmethyl)thioureido]-3-(1H-indol-3-yl)propionic acid methyl ester citrate, polar diastereoisomer

In the manner described for Example 41, the polar diastereoisomer of 2-[3-(4-dimethylamino-4-phenylcyclohexylmethyl)thioureido]-3-(1H-indol-3-yl)propionic acid methyl ester was also obtained in the form of a light-yellow solid (157 mg, m.p. 228–234° C.). 156 mg thereof (0.603 mmol.) were converted analogously to Example 41 into 197 mg of the corresponding citrate (light-yellow solid, m.p. 167–172° C.).

Measurement of ORL1 Binding

The cyclohexane derivatives of the general formula I were investigated in a receptor binding assay with $^3$H-nociceptin/orphanin FQ with membranes of recombinant CHO-ORL1 cells. This test system was conducted in accordance with the method described by Ardati et al. (Mol. Pharmacol., 51, 1997, p. 816–824). The concentration of $^3$H-nociceptin/orphanin FQ in these experiments was 0.5 nM. The binding assays were carried out with in each case 20 μg of membrane protein per 200 μl batch in 50 mM Hepes, pH 7.4, 10 mM MgCl$_2$ and 1 mM EDTA. The binding to the ORL1 receptor was determined using in each case 1 mg of WGA-SPA beads (Amersham-Pharmacia, Freiburg), by incubation of the batch for one hour at RT and subsequent measurement in a Trilux scintillation counter (Wallac, Finland). The affinity is indicated in Table 1 as the nanomolar $K_i$ value or % inhibition at c=1 µM.

Measurement of µ Binding

The receptor affinity for the human µ-opiate receptor was determined in a homogeneous batch on microtitre plates. To that end, serial dilutions of the particular substituted cyclohexane derivative to be tested were incubated for 90 minutes at room temperature with a receptor membrane preparation (15–40 µg of protein per 250 µl of incubation batch) of CHO-K1 cells, which express the human µ-opiate receptor (RB-HOM receptor membrane preparation from NEN, Zaventem, Belgium), in the presence of 1 nmol./l of the radioactive ligand [$^3$H]-naloxone (NET719, NEN, Zaventem, Belgium) and 1 mg of WGA-SPA beads (wheatgerm agglutinin SPA beads from Amersham/Pharmacia, Freiburg, Germany) in a total volume of 250 µl. The incubation buffer used was 50 mmol./l of Tris-HCl supplemented with 0.05 wt. % sodium azide and with 0.06 wt. % bovine serum albumin. In order to determine non-specific binding, 25 µmol./l of naloxone were additionally added. When the ninety-minute incubation time was complete, the microtitre plates were centrifuged off for 20 minutes at 1000 g and the radioactivity was measured in a β-counter (Microbeta-Trilux, PerkinElmer Wallac, Freiburg, Germany). The percentage displacement of the radioactive ligand from its binding to the human µ-opiate receptor at a concentration of the test substances of 1 µmol./l was determined and stated as the percentage inhibition (% inhibition) of specific binding. In some cases, starting from the percentage displacement, $IC_{50}$ inhibitory concentrations, which effect 50% displacement of the radioactive ligand, were calculated by means of different concentrations of the compounds of the general formula I to be tested. Ki values for the test substances were obtained by conversion by means of the Cheng-Prusoff equation.

Analgesia Test in the Tail-flick Test in the Mouse

The mice were each placed individually into a test cage and the base of the tail was exposed to the focused heat ray of an electric lamp (tail-flick type 50/08/1. bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention, or of the particular comparison solutions, the mice were pre-tested twice in the course of five minutes and the mean of those measurements was calculated as the pre-test mean.

The solutions of the compound of the general formula I according to the invention and the comparison solutions were then administered intravenously. Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)] \times 100$$

where time $T_0$ is the latency before administration, time $T_1$ is the latency after administration of the active ingredient combination and time $T_2$ is the maximum exposure time (12 seconds).

TABLE 1

| Example No. | ORL1 Ki [nM] or % inhibition [1 µM] | µ Ki [nM] or % inhibition [1 µM] | Tail flick (mouse, i.v.) % inhibition (dose [mg/kg]) |
|---|---|---|---|
| 1 | 2.8 | 2.6 | |
| 2 | 86 | | |
| 3 | 6.8 | 19 | |
| 4 | 19 | 74 | |
| 5 | 7.8 | 36 | |
| 6 | 3.6 | 15 | |
| 7 | 3.8 | 8 | |
| 8 | 21 | 6.4 | |
| 9 | 59 | 2.6 | 97 (10) |
| 10 | 27 | 15 | 52 (10) |
| 11 | 6.6 | 5.8 | 100 (10) |
| 12 | 20 | 5.2 | 70 (3.16) |
| 13 | 30 | 14 | |
| 14 | 1.8 | 0.6 | 92 (10) |
| 15 | 60 | 85% | |
| 16 | 13 | 51 | |
| 17 | 10 | 9.1 | |
| 18 | 1.2 | 3.6 | |
| 19 | 50% | 55 | |
| 20 | 40 | 27 | |
| 21 | 53 | 23 | |
| 22 | 54 | 17 | |
| 23 | 90 | 11 | |
| 24 | 2.5 | 1.6 | |
| 25 | 68% | 36 | |
| 26 | 87 | 120 | |
| 27 | 51 | 9.3 | |
| 28 | 12 | 24 | |
| 29 | 7.9 | 1 | |
| 30 | 37 | 11 | |
| 31 | 18 | 6.1 | |
| 32 | 8.9 | 3.3 | |
| 33 | 43 | 11 | |
| 34 | 6.9 | 0.9 | |
| 35 | 51% | 48 | |
| 36 | 58 | 27 | |
| 37 | 52% | 15 | |
| 38 | 92 | 70 | |
| 39 | 24 | 6.2 | |
| 40 | 2.5 | 0.8 | |
| 41 | 59% | 93 | |
| 42 | 39 | 33 | |

Parental Solution of a 4-aminomethyl-1-aryl-cyclohexylamine Derivative According to the Invention 38 g of one of the 4-aminomethyl-1-aryl-cyclohexylamine derivatives according to the invention, here Example 1, are dissolved in 1 l of water for injection purposes at room temperature and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:

1. A 4-aminomethyl-1-aryl-cyclohexylamine compound corresponding to formula I

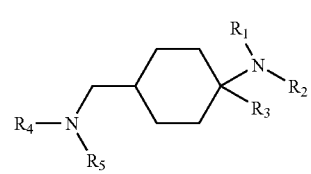

I wherein
R¹ and R², independently of one another, represent H, methyl or ethyl, provided R¹ and R² may not simultaneously be H, or the radicals R¹ and R² together form a ring and represent (CH₂)₅, R³ represents $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-4}$-alkyl group and in each case unsubstituted or mono- or poly-substituted, R⁴ represents H, $C_{1-8}$-alkyl, saturated or unsaturated, branched or unbranched, mono- or poly-substituted or unsubstituted; or $C(X)R^7$, $C(X)NR^7R^8$, $C(X)OR^9$, $C(X)SR^9$, $S(O_2)R^9$, wherein X=O or S, wherein R⁷ represents H; $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-6}$-alkyl group and in each case unsubstituted or mono- or poly-substituted, R⁸ represents H, $C_{1-4}$-alkyl, saturated or unsaturated, branched or unbranched, mono- or poly-substituted or unsubstituted, or the radicals R⁷ and R⁸ together form a ring and represent $CH_2CH_2OCH_2CH_2$, 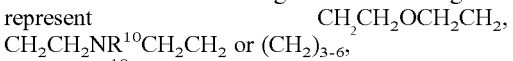 $CH_2CH_2NR^{10}CH_2CH_2$ or $(CH_2)_{3-6}$, wherein R¹⁰ represents H; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl and in each case mono- or poly-substituted or unsubstituted, R⁹ represents $C_{1-8}$-alkyl or $C_{3-8}$-cycloalkyl, in each case saturated or unsaturated, branched or unbranched, mono- or poly-substituted or unsubstituted; aryl or heteroaryl, in each case unsubstituted or mono- or poly-substituted; aryl, $C_{3-8}$-cycloalkyl or heteroaryl bonded via a saturated or unsaturated, branched or unbranched, substituted or unsubstituted $C_{1-4}$-alkyl group and in each case unsubstituted or mono- or poly-substituted, R⁵ represents H; $C_{3-8}$-cycloalkyl, aryl or heteroaryl, in each case unsubstituted or mono- or poly-substituted; a cycloalkyl, a cycloalkyl, aryl or heteroaryl group bonded via a branched or unbranched, substituted or unsubstituted $C_{1-6}$-alkyl group and in each case substituted or unsubstituted, wherein R⁴ and R⁵ do not simultaneously represent H,
or R⁴ and R⁵ together form a heterocyclic ring having from 3 to 8 atoms in the ring, saturated or unsaturated, mono- or poly-substituted or unsubstituted, in the form of a racemate or a pure stereoisomer or a mixture of stereoisomers in any mixing ratio,
or a solvate thereof or a salt thereof with a physiologically tolerated acid.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a solvate.

7. The compound of claim 6, wherein said solvate is a hydrate.

8. The compound of claim 1, wherein R⁴ and R⁵ together form a heterocydic ring having from 3 to 8 atoms in the ring, saturated or unsaturated, mono- or poly-substituted or unsubstituted, which is condensed with further rings.

9. The compound of claim 1, wherein R¹ and R², independently of one another, represent CH₃ or H, and R¹ and R² do not simultaneously represent H.

10. The compound of claim 1, wherein R³ represents $C_{3-8}$-cycloalkyl, aryl or heteroaryl, in each case unsubstituted or mono- or poly-substituted; aryl, $C_{3-8}$-cycloalkyl or heteroaryl bonded via a saturated or unsaturated, unbranched, substituted or unsubstituted $C_{1-2}$-alkyl group and in each case unsubstituted or mono- or poly-substituted.

11. The compound of claim 1, wherein R³ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or poly-substituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or poly-substituted.

12. The compound of claim 1, wherein R³ represents phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or poly-substituted; phenyl, furyl or thiophenyl bonded via a saturated, unbranched $C_{1-2}$-alkyl group and in each case unsubstituted or mono- or poly-substituted.

13. The compound of claim 1, wherein R³ represents phenyl, thiophenyl, pyridyl or benzyl, in each case substituted or unsubstituted, particularly preferably phenyl.

14. The compound of claim 1, wherein R⁴ represents H, $C(X)R^7$, $C(X)NR^7R^8$, $C(X)OR^9$, $C(X)SR^9$ or $S(O_2)R^9$, wherein X=O or S.

15. The compound of claim 1, wherein R⁴ represents H, $C(X)R^7$ or $C(X)NR^7R^8$ wherein X=O or S.

16. The compound of claim 1, wherein R⁴ represents H or $C(O)R^7$; $CONR^7R^8$ or $CSNR^7R^8$.

17. The compound of claim 1, wherein R⁸ represents H and R⁷ represents a heteroaryl or aryl group bonded via a $C_{1-6}$-alkyl group.

18. The compound of claim 1, wherein R⁸ represents H and R⁷ represents phenyl, naphthyl, pyridyl, benzothiophenyl, benzofuranyl, quinolinyl, isoquinolinyl, benzothiazolyl, indolyl or indanyl, in each case substituted or unsubstituted.

19. The compound of claim 1, wherein R⁸ represents H and R⁷ represents phenyl or indolyl, in each case substituted or unsubstituted.

20. The compound of claim 1, wherein R⁴ and R⁵ together form a heterocyclic ring having from 3 to 8 atoms in the ring, saturated or unsaturated; mono- or poly-substituted or unsubstituted, of which, in addition to the compulsory N, from 0 to 1 further hetero atoms, selected from N, S and O, are present in the ring.

21. The compound of claim 1, wherein $R^4$ and $R^5$ together form a heterocycic ring having from 5 to 7 atoms in the ring, of which, in addition to the compulsory N, from 0 to 1 further hetero atoms, selected from N, S and O, are present in the ring.

22. The compound of claim 1, wherein $R^4$ and $R^5$ together form a heterocyclic ring which is condensed with aromatic or heteroaromatic rings, these rings being optionally condensed with further aromatic or heteroaromatic rings.

23. The compound of claim 1, wherein $R^5$ represents H, $C_{3-8}$-cycloalkyl, aryl or heteroaryl, in each case unsubstituted or mono- or poly-substituted.

24. The compound of claim 1, wherein $R^5$ represents H, cyclobutyl, cyclopropyl, cyclopentyl, cyclohexyl, cycloheptyl, cyclooctyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthyl, pyrazolinonyl, oxopyrazolinonyl, dioxolanyl, quinolinyl, isoquinolinyl, phthalazinyl or quinazolinyl, in each case unsubstituted or mono- or poly-substituted.

25. The compound of claim 1, wherein $R^5$ represents H, cyclopentyl, cyclohexyl, indolyl, naphthyl, benzofuranyl, benzothiophenyl, indanyl, phenyl, thiophenyl, furyl and pyridyl, in each case unsubstituted or mono- or poly-substituted.

26. The compound of claim 1, wherein $R^5$ represents an aryl or heteroaryl group bonded via a $C_{1-6}$-alkyl group (which may be branched or unbranched, substituted or unsubstituted), which aryl or heteroaryl group in each case may be substituted or unsubstituted.

27. The compound of claim 26, wherein $R^5$ represents an aryl or heteroaryl group, said aryl or heteroaryl group being a phenyl, indolyl, naphthyl, benzofuranyl, benzothiophenyl, indanyl, thiophenyl, furyl, pyridyl, pyrrolyl, pyrazinyl, pyrimidyl, quinolinyl or isoquinolinyl group, in each case unsubstituted or mono- or poly-substituted.

28. The compound of claim 27, wherein said aryl or heteroaryl group is a phenyl or indolyl group, in each case unsubstituted or mono- or poly-substituted.

29. The compound of claim 1, wherein $R^5$ represents an aryl or heteroaryl group bonded via a branched or unbranched, substituted or unsubstituted $C_{1-6}$-alkyl group which is substituted by H, $C^{1-4}$-alkyl, saturated or unsaturated, branched or unbranched, mono- or poly-substituted or unsubstituted; or $C(O)O—C_{1-4}$-alkyl, saturated or unsaturated, branched or unbranched, mono- or poly-substituted or unsubstituted.

30. The compound of claim 29, wherein said $C_{1-6}$-alkyl group is substituted by H, $CH_3$, $C_2H_5$ or $C(O)O—CH_3$.

31. The compound of claim 29, wherein said $C_{1-6}$-alkyl group is substituted by H or $CH_3$.

32. The compound of claim 1, wherein said compound is selected from the group consisting of:

(4-{[(1H-indol-3-ylmethyl)amino]methyl}-1-phenylcyclohexyl)dimethylamine dihydrochioride, non-polar diastereoisomer, (4-{[(1H-indol-3-ylmethyl)amino]methyl}-1-phenylcyclohexyl)dimethylamine dihydrochloride, polar diastereoisomer, (4-{[2-(1H-indol-3-yl)-1-methylethylamino]methyl}-1-phenylcyclohexyl)dimethylamine dihydrochloride, non-polar diastereoisomer, (4-{[2-(1H-indol-3-yl)-1-methylethylamino]methyl}-1-phenylcyclohexyl)dimethylamine dihydrochloride, polar diastereoisomer, (4-{[2-(1H-indol-3-yl)ethylamino]methyl}-1-phenylcyclohexyl)dimethylamine dihydrochloride, non-polar diastereoisomer, (4-{[2-(1H-indol-3-yl)ethylamino]methyl}-1-phenylcyclohexyl)dimethylamine dihydrochloride, polar diastereoisomer, N-(4-dimethylamino-4-phenylcyclohexylmethyl)-4-(1H-indol-3-yl)-butyramide hydrochloride, non-polar diastereoisomer, N-(4-dimethylamino-4-phenylcyclohexylmethyl)-4-(1H-indol-3-yl)-butyramide hydrochloride, polar diastereoisomer, N-(4-dimethylamino-4-phenylcyclohexylmethyl)-2-(1H-indol-3-yl)-propionamide hydrochloride, non-polar diastereoisomer, 5-(1H-indol-3-yl)pentanoic acid (4-dimethylamino-4-phenylcyclohexylmethyl)amide hydrochloride, non-polar diastereoisomer, 6-(1H-indol-3-yl)hexanoic acid (4-dimethylamino-4-phenylcyclohexylmethyl)amide hydrochloride, non-polar diastereoisomer, N-(4-dimethylamino-4-phenylcyclohexylmethyl)-2-(1H-indol-3-yl)-acetamide hydrochloride, non-polar diastereoisomer, 5-(5-fluoro-1H-indol-3-yl)pentanoic acid (4-dimethylamino-4-phenylcyclohexylmethyl)amide citrate, non-polar diastereoisomer, 5-(5-fluoro-1H-indol-3-yl)pentanoic acid (4-dimethylamino-4-phenylcyclohexylmethyl)amide citrate, polar diastereoisomer, N-(4-dimethylamino-4-phenylcyclohexylmethyl)-2-indol-1-yl-acetamide, non-polar diastereoisomer, N-(4-dimethylamino-4-phenylcyclohexylmethyl)-2-indol-1-yl-acetamide, polar diastereoisomer, 6-(5-fluoro-1H-indol-3-yl)hexanoic acid (4-dimethylamino-4-phenylcyclohexylmethyl)amide citrate, polar diastereoisomer, 6-(5-fluoro-1H-indol-3-yl)hexanoic acid (4-dimethylamino-4-phenylcyclohexylmethyl)amide citrate, polar diastereoisomer, N-(4-dimethylamino-4-phenylcyclohexylmethyl)-3-indol-1-yl-propionamide citrate, non-polar diastereoisomer, N-(4-dimethylamino-4-phenylcyclohexylmethyl)-3-indol-1-yl-propionamide citrate, polar diastereoisomer, 4-(5-fluoro-1H-indol-3-yl)butanoic acid (4-dimethylamino-4-phenylcyclohexylmethyl)amide hydrochloride, non-polar diastereoisomer, 4-(5-fluoro-1H-indol-3-yl)butanoic acid (4-dimethylamino-4-phenylcyclohexylmethyl)amide hydrochloride, polar diastereoisomer, 6-(5-chloro-1H-indol-3-yl)hexanoic acid (4-dimethylamino-4-phenylcyclohexylmethyl)amide hydrochloride, non-polar diastereoisomer, 6-(5-chloro-1H-indol-3-yl)hexanoic acid (4-dimethylamino-4-phenyl-cyclohexylmethyl)amide hydrochloride, polar diastereoisomer, N-(4-dimethylamino-4-phenylcyclohexyl)-2-(5-fluoro-2-methyl-1H-indol-3-yl)acetamide citrate, non-polar diastereoisomer, N-(4-dimethylamino-4-phenylcyclohexyl)-2-(5-fluoro-2-methyl-1H-indol-3-yl)acetamide citrate, polar diastereoisomer,
1-(4-dimethylamino-4-phenylcyclohexylmethyl)-3-(3-phenylpropyl)urea hydrochloride, non-polar diastereoisomer,
1-(4-dimethylamino-4-phenylcyclohexylmethyl)-3-(3-phenylpropyl)urea hydrochloride, polar diastereoisomer,
1-(4-dimethylamino-4-phenylcyclohexylmethyl)-3-[2-(1H-indol-3-yl)ethyl]urea hydrochloride, polar diastereoisomer,
1-(4-dimethylamino-4-phenylcyclohexylmethyl)-3-[2-(1H-indol-3-yl)ethyl]urea, non-polar diastereoisomer,
1-(4-dimethylamino-4-phenylcyclohexylmethyl)-3-[2-(1H-indol-3-yl)-1-methylethyl]urea hydrochloride, non-polar diastereoisomer,
1-(4-dimethylamino-4-phenylcyclohexylmethyl)-3-[2-(1H-indol-3-yl)-1-methylethyl]urea hydrochloride, polar diastereoisomer,
1-(4-dimethylamino-4-phenylcyclohexylmethyl)-3-[2-(5-fluoro-1H-indol-3-yl)ethyl]urea citrate, polar diastereoisomer,
1-(4-dimethylamino-4-phenylcyclohexylmethyl)-3-[2-(5-fluoro-1H-indol-3-yl)ethyl]urea citrate, non-polar diastereoisomer,
4-(5-fluoro-1H-indol-3-yl)piperidine-1-carboxylic acid (4-dimethylamino-4-phenylcyclohexylmethyl)amide citrate, non-polar diastereoisomer,
4-(5-fluoro-1H-indol-3-yl)piperidine-1-carboxylic acid (4-dimethylamino-4-phenylcyclohexylmethyl)amide citrate, polar diastereoisomer,
4-(5-methoxy-1H-indol-3-yl)piperidine-1-carboxylic acid (4-dimethylamino-4-phenylcyclohexylmethyl) amide citrate, non-polar diastereoisomer,
4-(5-methoxy-1H-indol-3-yl)piperidine-1-carboxylic acid (4-dimethylamino-4-phenylcyclohexylmethyl) amide citrate, polar diastereoisomer,
1-(4-dimethylamino-4-phenylcyclohexylmethyl)-3-[2-(1H-indol-3-yl)ethyl]thiourea citrate, polar diastereoisomer,
1-(4-dimethylamino-4-phenylcyclohexylmethyl)-3-[2-(1H-indol-3-yl)ethyl]thiourea citrate, non-polar diastereoisomer,
2-[3-(4-dimethylamino-4-phenylcyclohexylmethyl)thioureido]-3-(1H-indol-3-yl)propionic acid methyl ester citrate, polar diastereoisomer, and
2-[3-(4-dimethylamino-4-phenylcyclohexylmethyl)thioureido]-3-(1H-indol-3-yl)propionic acid methyl ester citrate, non-polar diastereoisomer, or a mixture of any of the foregoing.

33. A pharmaceutical formulation comprising as an active ingredient a pharmaceutically effective amount of at least one 4-ammomethyl-1-aryl-cyclohexylamine compound according to claim 1 and a pharmaceutically acceptable carrier or adjuvant.

34. A method of alleviating pain in a mammal, said method comprising inhibiting the opiod-receptor-like 1 receptor ("ORL-1") administering to said mammal an effective pain alleviating amount of a 4-aminomethyl-1-aryl-cyclohexylamine compound according to claim 1.

35. The method of claim 34 wherein said pain is acute, visceral, neuropathic or chronic pain.

36. A process for preparing a compound according to claim 1, comprising:
reacting a 4-aminocyclohexanecarbaldehyde with an amine in the presence of a reducing agent.

37. The process of claim 36, wherein said reducing agent is sodium borohydride.

38. The process of claim 36, further comprising the step of reacting a resulting compound with a carboxylic acid or sulfonic acid chloride or an anhydride in the presence of a base.

39. The process of claim 38, wherein said base is triethylamine.

40. A process for preparing a compound according to claim 1, comprising:
reacting a 4-aminocyclohexanecarbaldehyde with hydroxylamine to form an oxime,
reducing the oxime with a reducing agent, in the presence of a base, and
reacting the product with a carboxylic acid or sulfonic acid chloride or an anhydride in the presence of a second base.

41. The process of claim 40, wherein said reducing agent is lithium aluminium hydride, which is optionally ailkylated with $R^5X$, wherein X represents halide.

42. The process of claim 40, wherein said second base is triethylamine.

43. A process for preparing a 4-aminomethyl-1-aryl-cyclohexylamine compound according to claim 1, comprising:
converting one of two amine components to be linked, $HNR^7R^8$ or

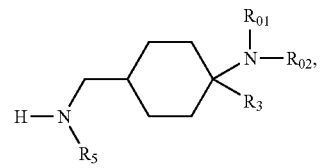

into a chloroformic acid ester and reacting the chloroformic acid ester with a second amine component.

44. The process of claim 43 wherein said chloroformic acid ester is a phenyl ester.

45. A process for preparing a 4-aminomethyl-1-aryl-cyclohexylamine compound according to claim 1, comprising:
converting one of two amine components to be linked, $HNR^7R^8$ or

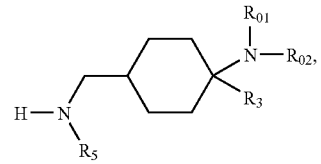

into an isothiocyanate with thiophosgene and reacting the isothiocyanate with a second amine component.

46. A process for preparing a 4-aminocyclohexanecarbaldehyde compound according to claim 1, comprising:
reacting a 4-aminocyclohexanone compound with methoxytriphosphonium chloride and a base and then with aqueous acid.

47. The process of claim 46, wherein said base is sodium hydride.

48. The process of claim 46, wherein said aqueous acid is HCl.

49. A method of treating anxiety, said method comprising administering a pharmaceutically effective amount of a 4-aminomethyl-1-aryl-cyclohexylamine compound according to claim 1.

* * * * *